(12) United States Patent
Nakahira et al.

(10) Patent No.: US 9,341,584 B2
(45) Date of Patent: May 17, 2016

(54) CHARGED-PARTICLE MICROSCOPE DEVICE AND METHOD FOR INSPECTING SAMPLE USING SAME

(75) Inventors: Kenji Nakahira, Fujisawa (JP); Atsushi Miyamoto, Yokohama (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 1182 days.

(21) Appl. No.: 13/379,663

(22) PCT Filed: Jun. 18, 2010

(86) PCT No.: PCT/JP2010/004071
§ 371 (c)(1),
(2), (4) Date: Dec. 21, 2011

(87) PCT Pub. No.: WO2011/039908
PCT Pub. Date: Apr. 7, 2011

(65) Prior Publication Data
US 2012/0098952 A1    Apr. 26, 2012

(30) Foreign Application Priority Data

Sep. 30, 2009 (JP) .................... 2009-225855

(51) Int. Cl.
*G01N 23/225* (2006.01)
*H01J 37/26* (2006.01)
(Continued)

(52) U.S. Cl.
CPC ........ *G01N 23/2251* (2013.01); *G01N 23/2255* (2013.01); *G06T 5/001* (2013.01); *H01J 37/265* (2013.01); *H01J 37/28* (2013.01); *G06T 2207/10061* (2013.01); *G06T 2207/20012* (2013.01); *G06T 2207/20021* (2013.01); *G06T 2207/30148* (2013.01); *H01J 2237/221* (2013.01); *H01J 2237/2815* (2013.01); *H01J 2237/2817* (2013.01)

(58) Field of Classification Search
CPC .................................................. G01N 23/2251
See application file for complete search history.

(56) References Cited

U.S. PATENT DOCUMENTS

| 5,043,570 A | 8/1991 | Takabayashi |
| 5,402,410 A * | 3/1995 | Yoshimura et al. ........ 369/275.1 |
| 2005/0100205 A1 | 5/2005 | Shishido et al. |

(Continued)

FOREIGN PATENT DOCUMENTS

| JP | 63-211472 | 9/1988 |
| JP | 3-44613 | 2/1991 |

(Continued)

OTHER PUBLICATIONS

Yaron I. Gold, et al., SEM Image Sharpening by Reversing the Effect on Non-ideal Beam Spot, SPIE pp. 620-624, Vol. Applied Materials/Opal, Nes Ziona, Israel.

*Primary Examiner* — James Pontius
(74) *Attorney, Agent, or Firm* — Baker Botts L.L.P.

(57) ABSTRACT

A high-performance image quality improvement process, capable of improving the image quality of low-definition areas (lower layer patterns in a multilayer, bottoms of holes in a hole pattern, etc.), is performed to a captured image. Definition enhancement intensity is calculated using height information included in design data or estimate values of sample height information calculated from the captured image, and the image quality improvement process is performed to the captured image using the definition enhancement intensity.

9 Claims, 27 Drawing Sheets

(51) Int. Cl.
*H01J 37/28* (2006.01)
*G06T 5/00* (2006.01)

(56) References Cited

U.S. PATENT DOCUMENTS

| | | | |
|---|---|---|---|
| 2006/0160037 A1* | 7/2006 | Brodsky et al. | 430/396 |
| 2006/0288325 A1 | 12/2006 | Miyamoto et al. | |
| 2008/0073523 A1* | 3/2008 | Takahashi et al. | 250/307 |
| 2008/0251719 A1 | 10/2008 | Nakahira et al. | |

FOREIGN PATENT DOCUMENTS

| | | |
|---|---|---|
| JP | 2004-219343 | 8/2004 |
| JP | 2006-351746 | 12/2006 |
| JP | 2006-351888 | 12/2006 |
| JP | 2007-214009 | 8/2007 |
| JP | 2008-177064 | 7/2008 |
| JP | 2009-198338 | 9/2009 |
| JP | 2009-245674 | 10/2009 |

* cited by examiner

FIG. 3
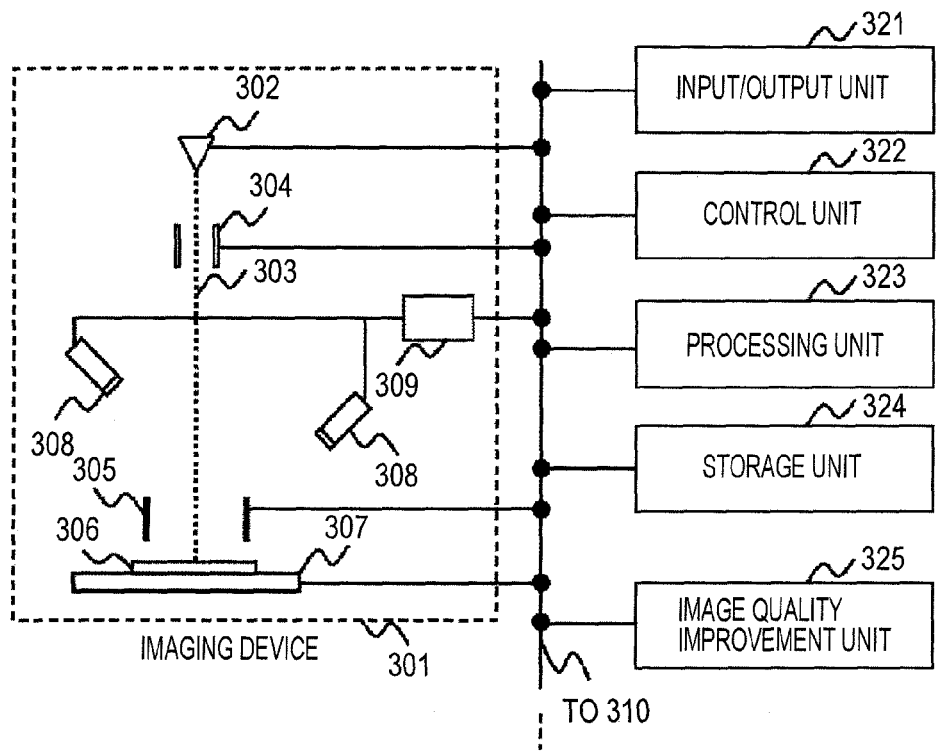
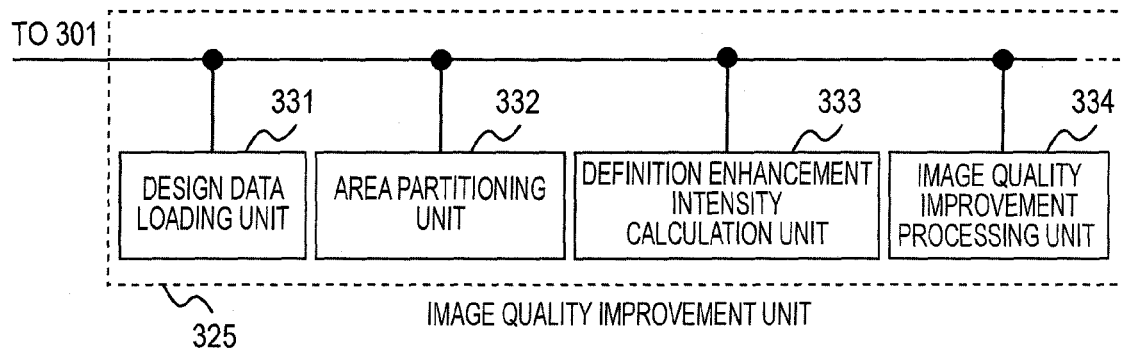

FIG. 9
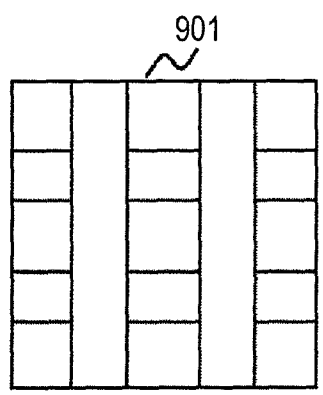
DESIGN DATA
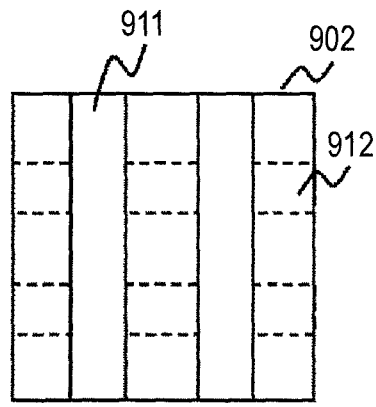
CAPTURED IMAGE
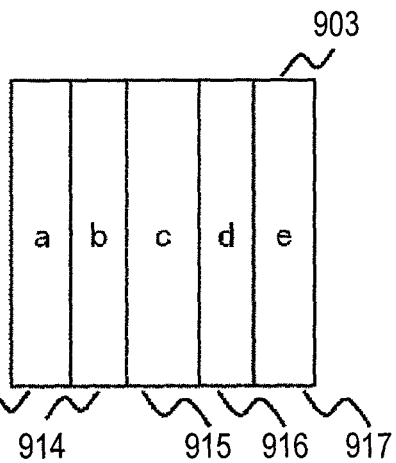
AREA PARTITIONING
RESULT 1
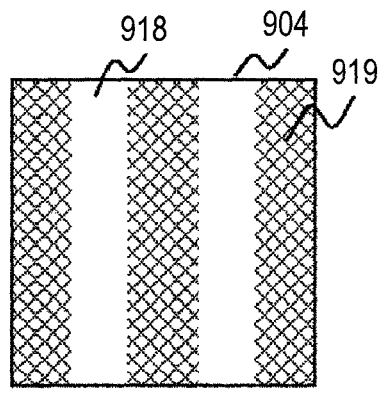
DEFINITION ENHANCEMENT
INTENSITY 1
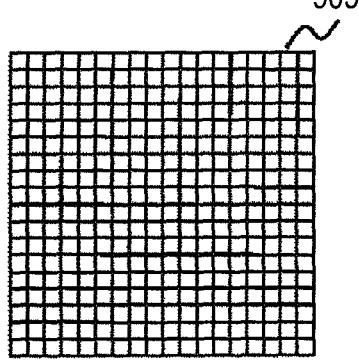
AREA PARTITIONING
RESULT 2
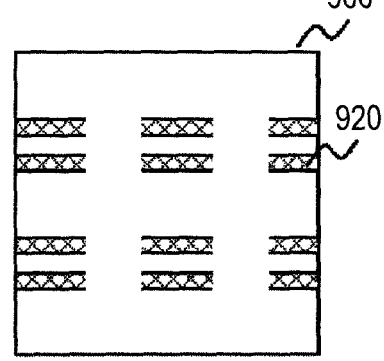
DEFINITION ENHANCEMENT
INTENSITY 2

FIG. 10
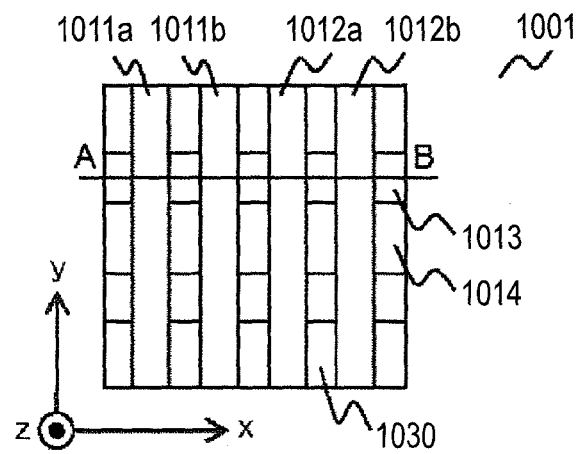
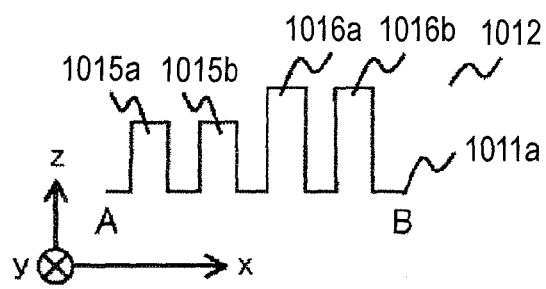
DESIGN DATA
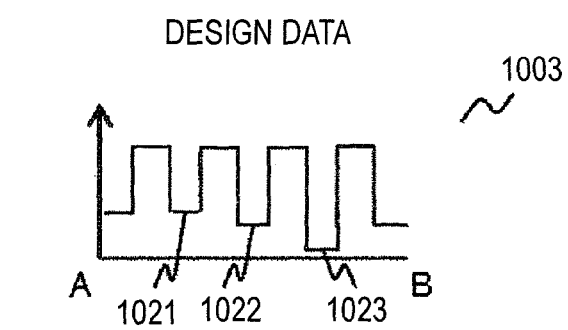
COUNT OF CHARGED PARTICLES
EMITTED FROM SAMPLE
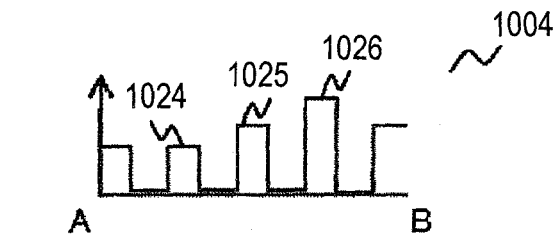
DEFINITION ENHANCEMENT INTENSITY

FIG. 27
- - - - - - CONTOUR OF DESIGN DATA
———— CONTOUR OF PATTERN CALCULATED FROM CAPTURED IMAGE
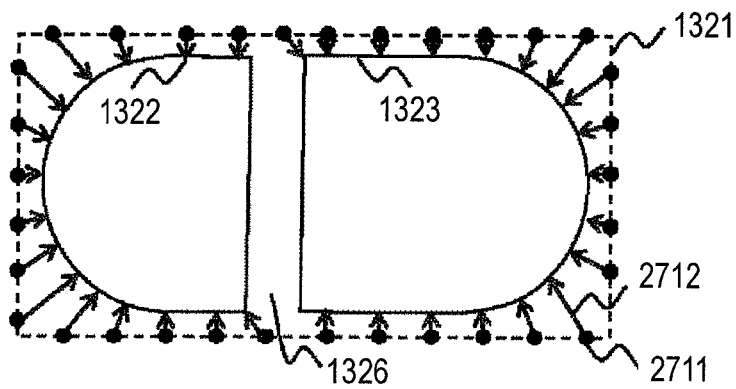
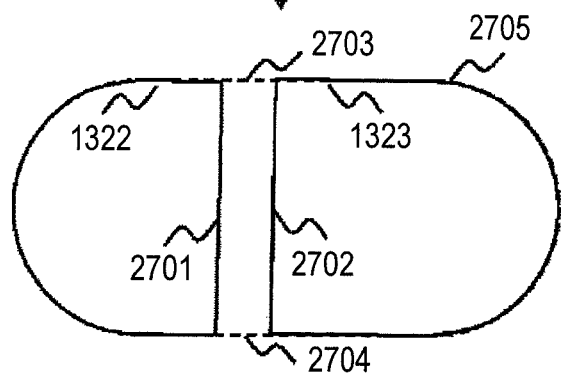
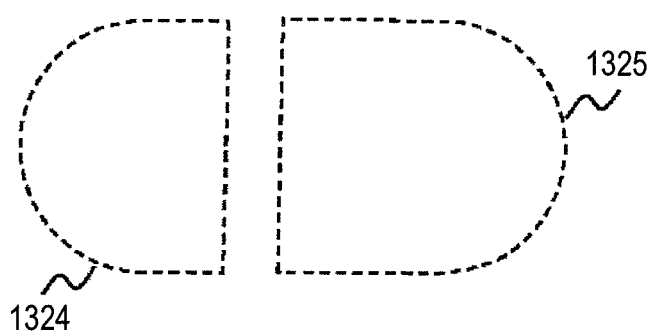

CHARGED-PARTICLE MICROSCOPE DEVICE AND METHOD FOR INSPECTING SAMPLE USING SAME

BACKGROUND ART

The present invention relates to a charged-particle microscope device which acquires images by irradiating a sample with charged particles and a method for inspecting a sample using the charged-particle microscope device. In particular, the present invention relates to a device and a method for performing an image quality improvement process to an acquired image of a sample by means of image processing and inspecting the sample by use of the processed image.

Charged-particle microscopes, having extremely high resolution compared to optical microscopes, are widely used for clearly and sharply observing microscopic structure of the observation object. A charged-particle microscope acquires a magnified image of a sample as the object by irradiating the sample with a charged particle beam and detecting particles (charged particles (of a type identical with or different from the irradiating charged particles), electromagnetic waves or photons) emitted from or passing through the sample.

Especially in semiconductor manufacturing processes, charged-particle microscopes (scanning electron microscopes, scanning ion microscopes, scanning transmission electron microscopes, etc.) are used for inspection of semiconductor wafers, measurement of pattern dimensions, measurement of pattern shapes, etc. For these purposes, inspections (observation of semiconductor patterns and defects, detection of defects, analysis of the cause of the defects, pattern dimension measurement, etc.) are carried out using images captured by a charged-particle microscope.

Providing high-quality images is one of the most important functions of the charged-particle microscopes. As described, for example, in Patent Literature 1, Patent Literature 2 and Non-patent Literature 1, image quality improvement processes have been proposed including an edge enhancement process, an image restoration process, a noise reduction process and a contrast correction process.

CITATION LIST

Patent Literature

Patent Literature 1: JP-A-63-211472
Patent Literature 2: JP-A-3-44613

Non-Patent Literature

Non-patent Literature 1: Y. I. Gold and A. Goldenshtein: Proc. SPIE, 3332, pp. 620-624 (1998)

SUMMARY OF INVENTION

With the progress of miniaturization and high density of semiconductor patterns in recent years, it is becoming more and more difficult to detect, by a required amount, particles emitted from lower layer patterns of a multilayer sample as an object of inspection. Accordingly, the visibility of the lower layer patterns becomes extremely low due to deterioration in the S/N, contrast, etc. Also for hole patterns, it is difficult to capture a fine image of an area at the bottom of a hole since the detection of charged particles emitted from the bottom of a hole is similarly difficult. While a larger amount of charged particles could be detected from lower layer patterns, bottoms of holes, etc. by improving hardware such as a charged-particle optical system and a detection system, such a scheme has limitations and dramatic improvement is difficult. Meanwhile, there are some methods in which improvement of software is performed, that is, captured images are subjected to image processing for improvement in image quality, thereby achieving fine visibility.

However, none of methods proposed in the Patent Literatures 1 and 2 and the Non-patent Literature 1 includes such image processing as may improve the definition (contrast, S/N, sharpness, resolution) of a complex pattern area for which achieving fine image quality is difficult (lower layer patterns, bottoms of holes in hole patterns, etc.) without deteriorating the image quality of the entire image. Further, the above methods do not include a process in which attention is directed to height information on the sample patterns.

Furthermore, the conventional methods perform, at most, an image quality improvement process using the captured image only or an image quality improvement process using the captured image and image capturing conditions (charged particle beam acceleration voltage, probe current, etc.) and do not perform a process of using design data. Here, the "design data" means data representing shape information on the semiconductor patterns to be manufactured. In many cases the shapes of the semiconductor patterns are described according to information on contours, etc. of the semiconductor patterns. The design data may include information on the properties of the sample (material properties, electrical properties, layer properties, etc.). Therefore, the conventional processes are sometimes incapable of achieving sufficient image quality improvement performance as listed below.

For example, the conventional processes are incapable of achieving sufficient visibility of areas for which the detection of particles emitted from the sample (area) is difficult (lower layer patterns in a multilayer, bottoms of holes in a hole pattern, etc.) without deteriorating the image quality of the entire image. A process for adjusting the contrast in regard to each local position (area) of an image (e.g., local contrast correction) has been proposed. Since the process, however, designed without taking into consideration how much to a great extent the particles emitted from each area of the sample are detectable, is incapable of accurately recognizing the lower layer patterns and the bottoms of holes and performing an appropriate definition enhancement process.

Further, when a plurality of lower layer patterns or hole patterns having similar properties are displayed in an image, execution of a process that causes great difference in the definition among the patterns can result in an unnatural image. In the conventional processes, it has been impossible to use the same or close values of definition enhancement intensity for such areas such that a natural image may be acquired. Furthermore, depending on the image, there are many cases where the user wants to designate an area whose visibility should particularly be improved. The conventional processes do not use an interface allowing the user to input such designation and cannot execute an appropriate process according to information that would be inputted through such an interface.

The present invention realizes an inspection device and an inspection method capable of sufficiently achieving an improvement in image quality for a captured image even in the aforementioned cases and conducting inspections (observation of sample patterns and defects, detection of defects, analysis of the cause of the defects, pattern dimension measurement, etc.) using the processed image.

Representative aspects of the present invention disclosed in this patent application can be summarized as follows:

(1) A method for inspecting a sample using a charged-particle microscope device, comprising: a captured image acquisition step of acquiring a captured image by irradiating the sample with charged particles and detecting particles of the same or different type emitted from the sample; an area partitioning step of partitioning the captured image into a plurality of local areas; an image processing step of executing image processing to the captured image partitioned into the plurality of local areas according to height information on the sample; and an inspection step of inspecting the sample using the image-processed captured image.

(2) The method for inspecting a sample using a charged-particle microscope device according to the aspect (1), further comprising a design data loading step of loading design data corresponding to the captured image acquired in the captured image acquisition step, wherein in the imaging step, height information on the sample acquired from the loaded design data is used as the height information on the sample.

(3) The method for inspecting a sample using a charged-particle microscope device according to the aspect (2), wherein in the image processing step, definition enhancement intensity is calculated for each of the local areas based on the height information on the sample acquired from the design data and the image processing of the captured image partitioned into the plurality of local areas is executed using the definition enhancement intensity.

(4) The method for inspecting a sample using a charged-particle microscope device according to the aspect (3), wherein in the calculation of the definition enhancement intensity, the definition enhancement intensity for a partitioned local area including at least one layer other than a top layer in the design data is calculated using layer information on layers existing above the layer under consideration. When each layer is irradiated with charged particles, part of particles emitted from the sample (irradiated layer) collide with a layer existing above the irradiated layer and are absorbed. Therefore, the amount of particles (emitted from the sample and) reaching the detector is greatly affected by the probability of the collision of a particle with an upper layer (higher layer). Thus, the degree (intensity) of the definition enhancement necessary for the layer as the target of processing can be judged properly by using the information on layers existing above the layer under consideration.

(5) The method for inspecting a sample using a charged-particle microscope device according to the aspect (1), wherein height information on the sample estimated from the captured image is used as the height information on the sample in the image processing step. By also using the design data in combination, an image quality improvement process of still higher performance becomes possible.

(6) A charged-particle microscope device comprising: charged-particle irradiation optical system means which irradiates a sample with charged particles; particle detection optical system means which detects particles of the same or different type emitted from the sample irradiated with the charged particles by the charged-particle irradiation optical system means; captured image acquisition means which acquires a captured image of the sample by processing a signal outputted by the particle detection optical system means; and image processing means which processes the captured image of the sample acquired by the captured image acquisition means, wherein the image processing means partitions the captured image into a plurality of local areas and executes image processing to the captured image partitioned into the plurality of local areas according to height information on the sample.

The present invention makes it possible to realize an inspection device and an inspection method capable of resolving the aforementioned problems of the conventional techniques and conducting inspections (observation of sample patterns and defects, detection of defects, analysis of the cause of the defects, pattern dimension measurement, etc.) by use of images to which a sufficient image quality improvement process has been performed.

These and other objects, features and advantages of the invention will be apparent from the following more particular description of preferred embodiments of the invention, as illustrated in the accompanying drawings.

BRIEF DESCRIPTION OF DRAWINGS

FIG. 3 shows the basic configuration of a charged-particle microscope in accordance with an embodiment of the present invention.

FIG. 9 is a schematic diagram showing an example of a method of area partitioning and a method of calculating definition enhancement intensity.

FIG. 10 is a schematic diagram showing an example of the calculation of the definition enhancement intensity using sample height information included in the design data.

FIG. 27 is a schematic diagram showing an example of the process of transforming the design data to make it fit with the captured image.

DESCRIPTION OF EMBODIMENTS

Figure 1:
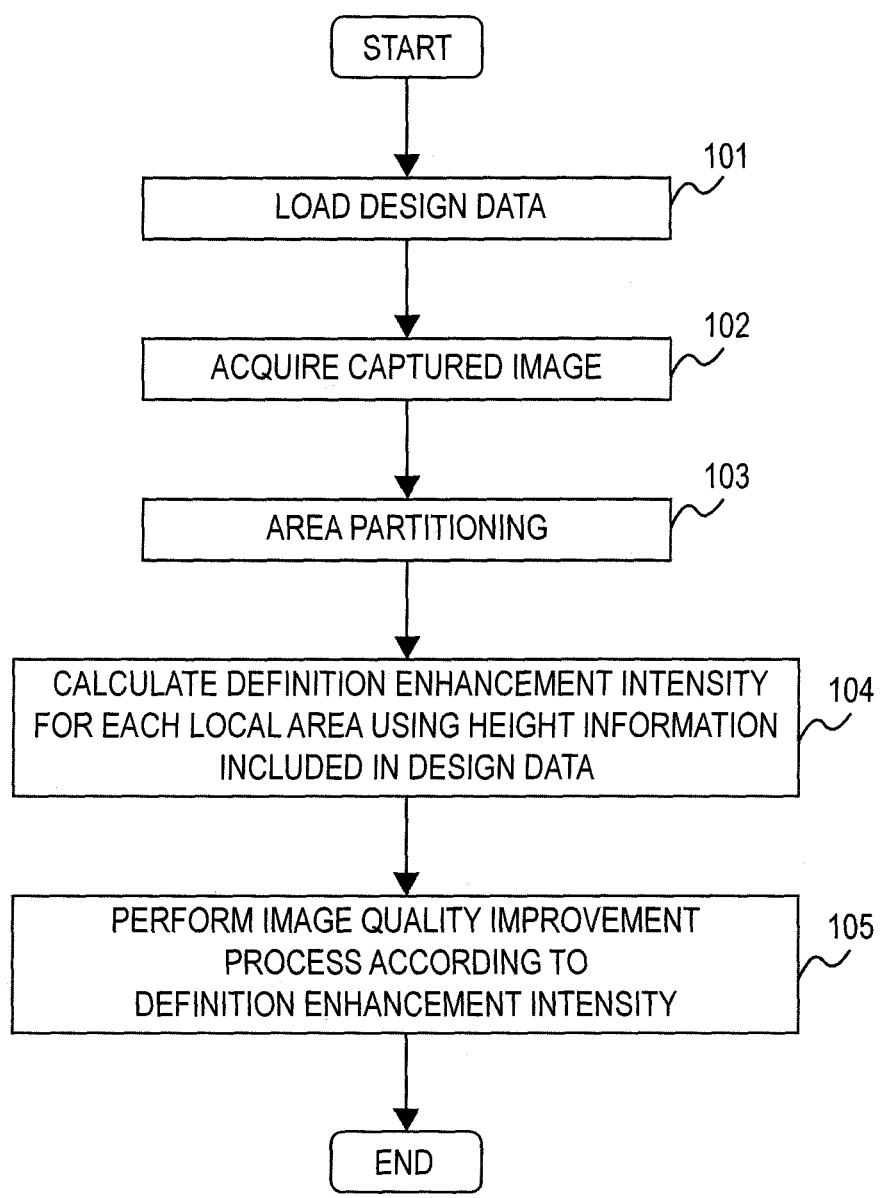
FIG. 1 is a flow chart showing a sequence of an image quality improvement process in accordance with the present invention.

FIG. 1 is a flow chart showing a sequence for acquiring a charged-particle image and performing an image quality improvement process in accordance with an embodiment of the present invention. In the first step 101, design data including information on a sample whose image should be captured is loaded. In step 102, a charged-particle image is acquired. The acquired charged-particle image will hereinafter be referred to as a "captured image". The step 102 may also be executed before the step 101. In the next step 103, the captured image is partitioned into a plurality of local areas. The step 103 may also be executed using the information included in the design data. Explanation of the local areas will be given later. In the next step 104, definition enhancement intensity is calculated for each local area using height information included in the design data. In step 105, the image quality improvement process is performed to the captured image according to the definition enhancement intensity. The output of the image quality improvement process will hereinafter be referred to as a quality-improved image. With the increase in the definition enhancement intensity, the image quality improvement process is performed with higher intensity so that the definition of the quality-improved image becomes higher.

By using the height information included in the design data, the amount of particles arriving at the detector (among the particles emitted from the sample) can be estimated. Thus, it is possible to automatically recognize low-visibility areas (a lower layer pattern of a multilayer, the bottom of a hole of a hole pattern, etc.) and thereby acquire an image in which the definition of the low-visibility areas has been increased without deteriorating the image quality of the other areas. The height information can either be a specific numerical value representing the distance from a certain reference point or information representing relative height relationship (just indicating whether each part is higher or lower than surrounding parts). Information indicating upper/lower layer relationship in a multilayer is also a type of the height information.

Figure 2:
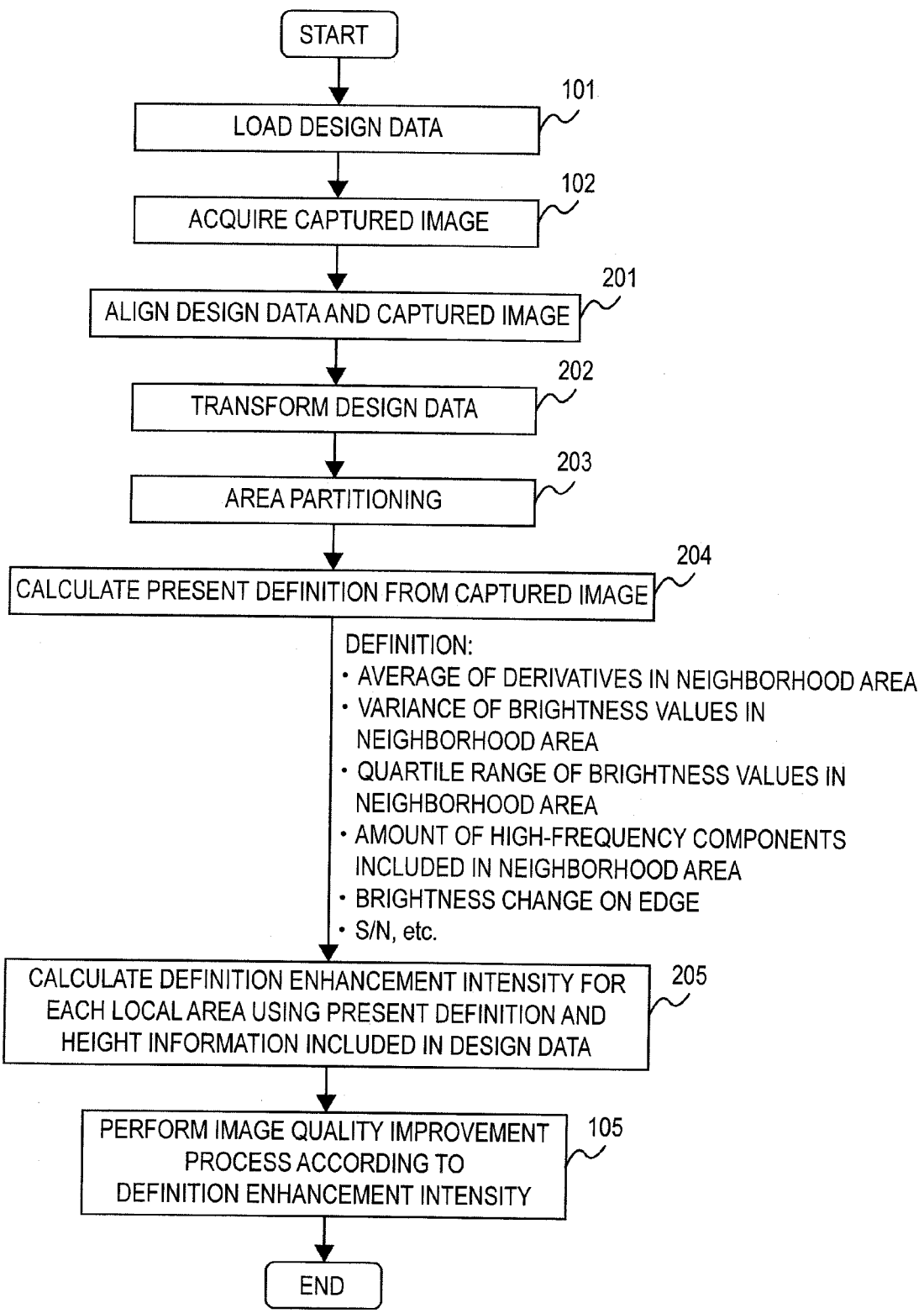
FIG. 2 is a flow chart showing a sequence of an image quality improvement process in accordance with the present invention.

FIG. 2 is a flow chart showing an embodiment different from the sequence of FIG. 1, wherein processes (steps) equivalent to those in FIG. 1 are assigned the same reference numerals as in FIG. 1. In the following explanation, equivalent processes, data, etc. will be indicated with the same reference numerals. Steps 101 and 102 in FIG. 2 are equivalent to those in FIG. 1. The steps 101 and 102 may also be executed in a different order. Since displacement generally occurs between the design data and the captured image, the loading of the design data in the step 101 is executed at least for a visual field larger than the visual field of the captured image to be acquired so that an area corresponding to the captured image can be covered by the design data even when the displacement has occurred. In the next step 201, alignment (positional adjustment) of the captured image and the design data is performed. In the next step 202, as need arises, the design data is transformed to make it fit with the captured image. The transformation of the design data will be explained in detail later. This step may be left out when the difference in the pattern shapes between the design data and the captured image is within a permissible range. Incidentally, the step 201 for the alignment of the captured image and the design data and the step 202 for transforming the design data as needed may also be executed in the same way after the step 102 in the sequence shown in FIG. 1. In the next step 203, the captured image is partitioned into a plurality of local areas. The step 203 may also be executed using the information included in the design data.

In the next step 204, definition in the captured image in the present state (hereinafter referred to as "present definition") is calculated. Here, the "definition" means an index representing at least one selected from the contrast, S/N, sharpness and resolution at each local position in the image. For example, the average of derivatives of the variation of brightness values (differential coefficients) in a local area including the targeted local position (hereinafter referred to as a "neighborhood area"), the variance of brightness values in the neighborhood area, the quartile range (the difference between the first quartile point and the third quartile point) of the brightness values in the neighborhood area, the intensity of high-frequency components included in the neighborhood area, the brightness change on an edge (line segment where the brightness value changes sharply), the S/N, etc. can be defined as the definition. However, the definition is not restricted to these examples. In the next step 205, the definition enhancement intensity is calculated for each local area using the present definition and the height information included in the design data. Thereafter, in the step 105, the image quality improvement process is performed according to the definition enhancement intensity, by which the quality-improved image is acquired. Here, the "definition enhancement intensity" means a value representing the degree of enhancement of the definition of the quality-improved image compared to the captured image.

Figure 12:
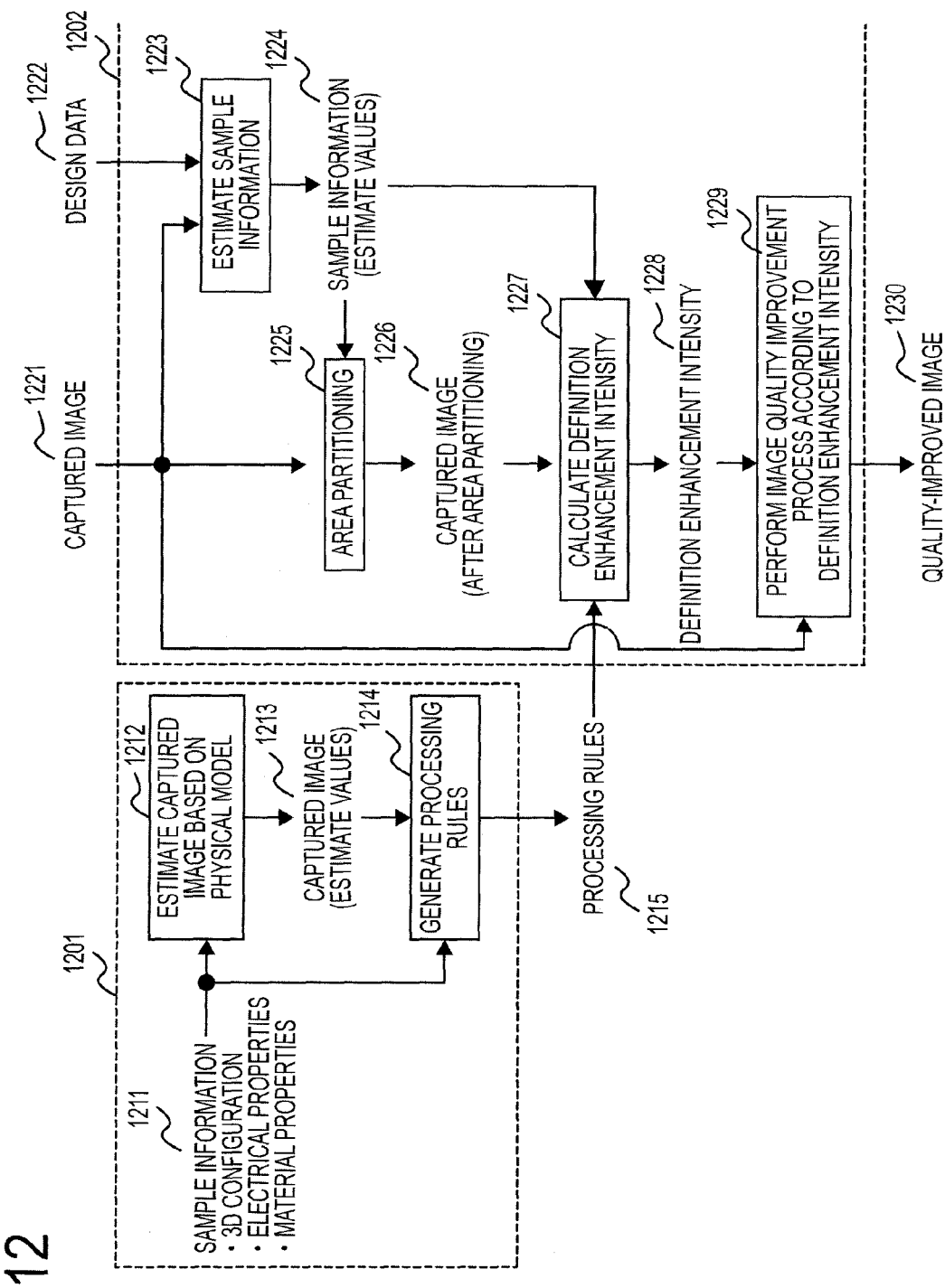
FIG. 12 is a schematic diagram showing a basic operation for acquiring a charged-particle image and performing the image quality improvement process.

FIG. 12 is a schematic diagram showing a basic operation for acquiring a charged-particle image and performing the image quality improvement process. First, before performing the image quality improvement process, processing rules 1215 to be used for the calculation of the definition enhancement intensity are generated by a sequence of processes indicated with a reference numeral 1201. Subsequently, by a sequence of processes indicated with a reference numeral 1202, the image quality improvement process is performed to the captured image, by which a quality-improved image 1230 is generated. In the process sequence 1201, various pieces of sample information 1211 that can be presumed are prepared first. The sample information can include height information on the sample, three-dimensional shape information (two-dimensional shape information and height information) on the sample, information indicating electrical properties of the sample, information indicating material properties of the sample, etc. In step 1212, a captured image is estimated for each piece of sample information 1211 based on a physical model regarding the imaging principles of the charged-particle microscope. By use of the sample information 1211 and the captured image estimate values 1213, it is possible to presume in which part of the image the definition drops. Therefore, the processing rules regarding how the definition enhancement intensity should be calculated can be designed appropriately. In step 1214, the processing rules 1215 are generated based on the sample information 1211 and the captured image estimate values 1213 as above.

The process sequence 1202 will be explained next. First, the sample information is estimated by step 1223. In this estimation, either the captured image 1221 or the design data 1222 may be used. For example, the height information and layer information included in the design data may directly be used as estimate values 1224 of the sample information. Further, the captured image is partitioned into local areas by step 1225. The step 1225 may also be executed using the sample information estimate values 1224. In the next step 1227, the definition enhancement intensity 1228 is calculated for each local area using the sample information estimate values 1224 according to the processing rules 1215 determined in the step (process sequence) 1201. In the final step 1229, the image quality improvement process is performed to the captured image according to the definition enhancement intensity.

The height information on the sample as the sample information has a strong relationship with the definition of the captured image as will be explained later. Further, whether the captured image is displayed clearly or not can be significantly affected by the electrical properties and the material properties in many cases. Since the definition of which area has to be enhanced with what intensity can be presumed by use of the sample information as explained above, an appropriate image quality improvement process can be performed.

FIG. 3 shows the basic configuration of a charged-particle microscope device in accordance with an embodiment of the present invention. The charged-particle microscope device is configured by properly using an imaging device 301, an input/output unit 321, a control unit 322, a processing unit 323, a storage unit 324, an image quality improvement unit 325, etc., for example. In the imaging device 301, a charged particle beam 303 is generated and emitted by a charged particle gun 302. The charged particle beam 303 passing through a condenser lens 304 and an object lens 305 is condensed and focused on the surface of the sample 306. It is possible to use two or more condenser lenses 304 and/or two or more object lenses 305. Subsequently, the captured image is acquired by detecting particles (charged particles, electromagnetic waves or photons) emitted from the sample 306 with a detector 308 and generating a digital image with an image generator 309 from a signal obtained by the detection. The captured image is stored in the storage unit 324 via a bus line 310. The detector 308 can be implemented by a photomultiplier, an APD (avalanche photodiode), etc. The number of detectors 308 may be one, or two or more. Detectors for detecting different types of particles (e.g., a detector for detecting electrons and a detector for detecting electromagnetic waves) may be combined properly. In the case of a SEM, detectors for detecting particles having different properties (e.g., a secondary electron detector and a backscattered electron detector) may be combined. In such cases where the charged-particle microscope device is equipped with two or more detectors, two or more captured images can generally be acquired by one image capturing (shooting). Images of the sample 306 at arbitrary positions can be acquired by moving a stage 307 which is in contact with the sample 306. This embodiment makes it possible to automatically recognize the areas needing the improvement of visibility by use of the information included in the design data and thereby acquire an image in which the image quality of such areas has been improved (by setting sufficiently high definition enhancement intensity for such areas) without deteriorating the image quality of the other areas.

The input/output unit 321 executes processes for the inputting of image capturing positions and image capturing conditions, the outputting of the captured images and the quality-improved images, etc. The control unit 322 executes processes for controlling the imaging device, such as adjustment of voltages applied to components like the charged particle gun 302, adjustment of focal positions of the condenser lens 304 and the object lens 305, control of the movement of the stage 307, and control of operation timing of the image generator 309. The control unit 322 controls also the input/output unit 321, the processing unit 323, the storage unit 324 and the image quality improvement unit 325. The processing unit 323 executes processes other than the image quality improvement process, such as a process related to automatic focusing which is necessary for correctly placing the focal point of the charged particle beam 303 on the surface of the sample 306. The processing unit 323 also executes measurement of lengths in the captured pattern, detection of defects, classification of the defects, etc. The storage unit 324 stores the captured images, the design data, the sample property information, the quality-improved images, and processing parameters for the image quality improvement, etc.

The image quality improvement unit 325 executes a sequence of processes shown in FIG. 1 for generating the quality-improved image from the captured image. The image quality improvement unit 325 is configured by properly using a design data loading unit 331 for executing the design data loading in the step 101, an area partitioning unit 332 for executing the area partitioning in the step 103, a definition enhancement intensity calculation unit 333 for executing the definition enhancement intensity calculation in the step 104, and an image quality improvement processing unit 334 for executing the image quality improvement process in the step 105. Incidentally, the design data loading by the design data loading unit 331 may be conducted either by loading the design data from the storage unit 324 previously storing the design data or by loading the design data from another device or file server via a network (although not shown in FIG. 3). While the design data loading unit 331 is included in the image quality improvement unit 325 in this example, the design data loading unit 331 may also be provided separately from the image quality improvement unit 325. Although not shown in FIG. 3, the image quality improvement unit 325 may be further equipped with an alignment unit for performing the alignment of the design data and the captured image in the step 201, a design data transformation unit for executing the design data transformation in the step 202, a present definition calculation unit for executing the present definition calculation in the step 204, etc.

Figure 4:
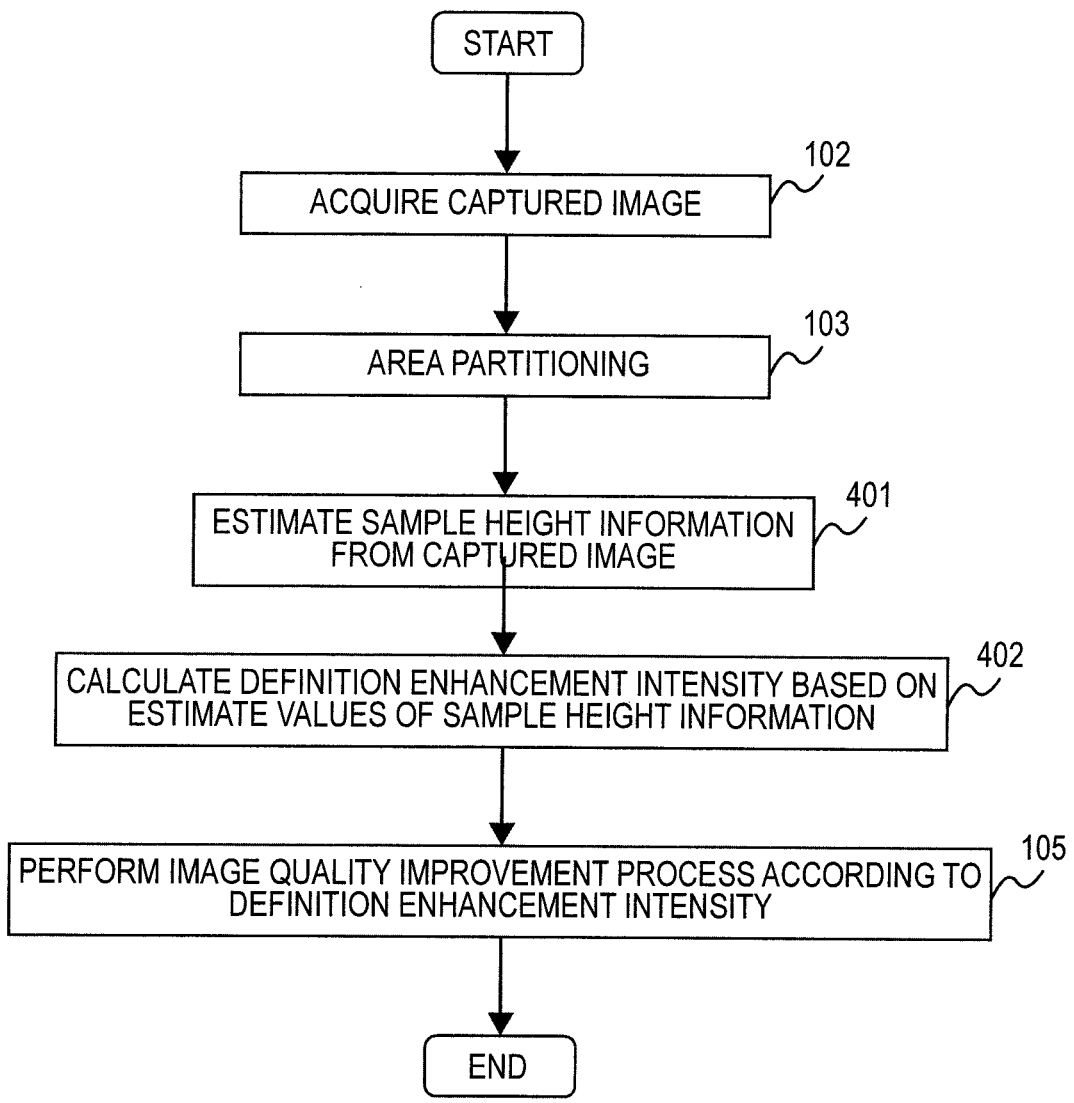
FIG. 4 is a flow chart showing a case where the image quality improvement process is performed without using information included in design data.

FIG. 4 is a flow chart showing a case where the image quality improvement process is performed without using the information included in the design data, as an embodiment different from the sequence of FIG. 1. The steps 102 and 103 in FIG. 4 are equivalent to those in FIG. 1. In the next step 401, the height information on the sample (sample height information) is estimated from the captured image. While the method for estimating the height information will be described later, it is possible, for example, to extract information on contours of the sample from the captured image and acquire the height information regarding the upper/lower layers of the patterns from information on how the contours intersect with each other. In the next step 402, the definition enhancement intensity is calculated based on estimate values of the sample height information. Finally, the image quality improvement process is performed according to the definition enhancement intensity in the step 105. Incidentally, it is also possible to execute the aforementioned step 204 (calculation of the present definition) between the steps 103 and 401 or between the steps 401 and 402 and calculate the definition enhancement intensity based on the present definition and the estimate values of the sample height information.

According to this example, even when no information included in the design data is inputted to the charged-particle microscope device or the definition should be increased for defects, etc. not described in the design data, the low-visibility areas can be recognized automatically by the estimation of the sample height information. Therefore, an image in which the definition of such areas has been improved without deteriorating the image quality of the other areas can be acquired. Further, it is also possible to execute a more high-performance image quality improvement process by using information included in the design data in combination.

Figure 5:
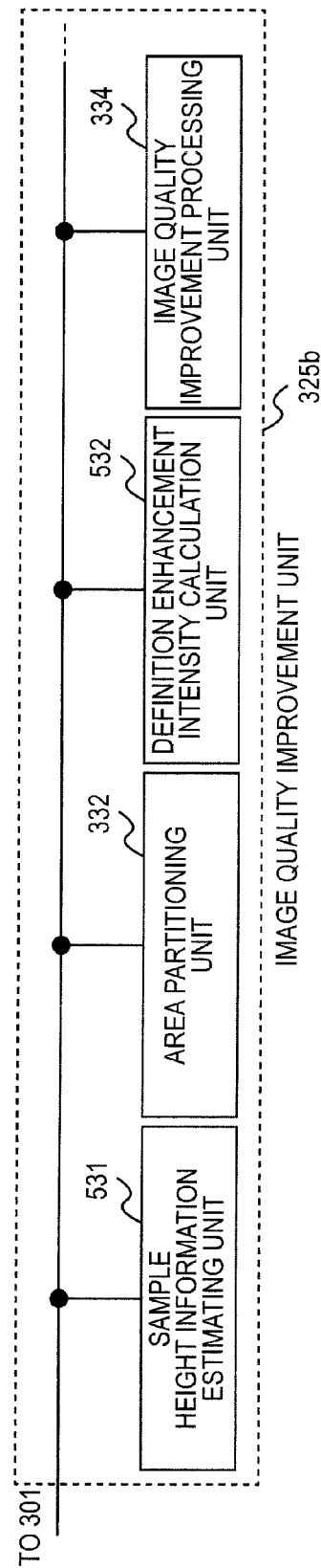
FIG. 5 is a block diagram showing an embodiment of an image quality improvement unit in a case where no design data is used.

FIG. 5 shows an embodiment of the image quality improvement unit in the case where no design data is used in the basic configuration shown in FIG. 3. The following explanation will be given only of the image quality improvement unit since the basic configuration of the imaging device 301, etc. is equivalent to that shown in FIG. 3. The image quality improvement unit 325b, configured differently from the image quality improvement unit 325 in FIG. 3, includes a sample height information estimating unit 531 for estimating the sample height information in the step 401 instead of the design data loading unit 331. Further, the image quality improvement unit 325b includes a definition enhancement intensity calculation unit 532 for calculating the definition enhancement intensity in the step 402. Incidentally, the image quality improvement unit 325b may be further equipped with the design data loading unit 331 for the case where the information included in the design data is used in combination. This embodiment makes it possible to automatically recognize the areas needing the improvement of visibility by use of information included in the captured image and thereby acquire an image in which the image quality of such areas has been improved (by setting sufficiently high definition enhancement intensity for such areas) without deteriorating the image quality of the other areas.

Figure 6:
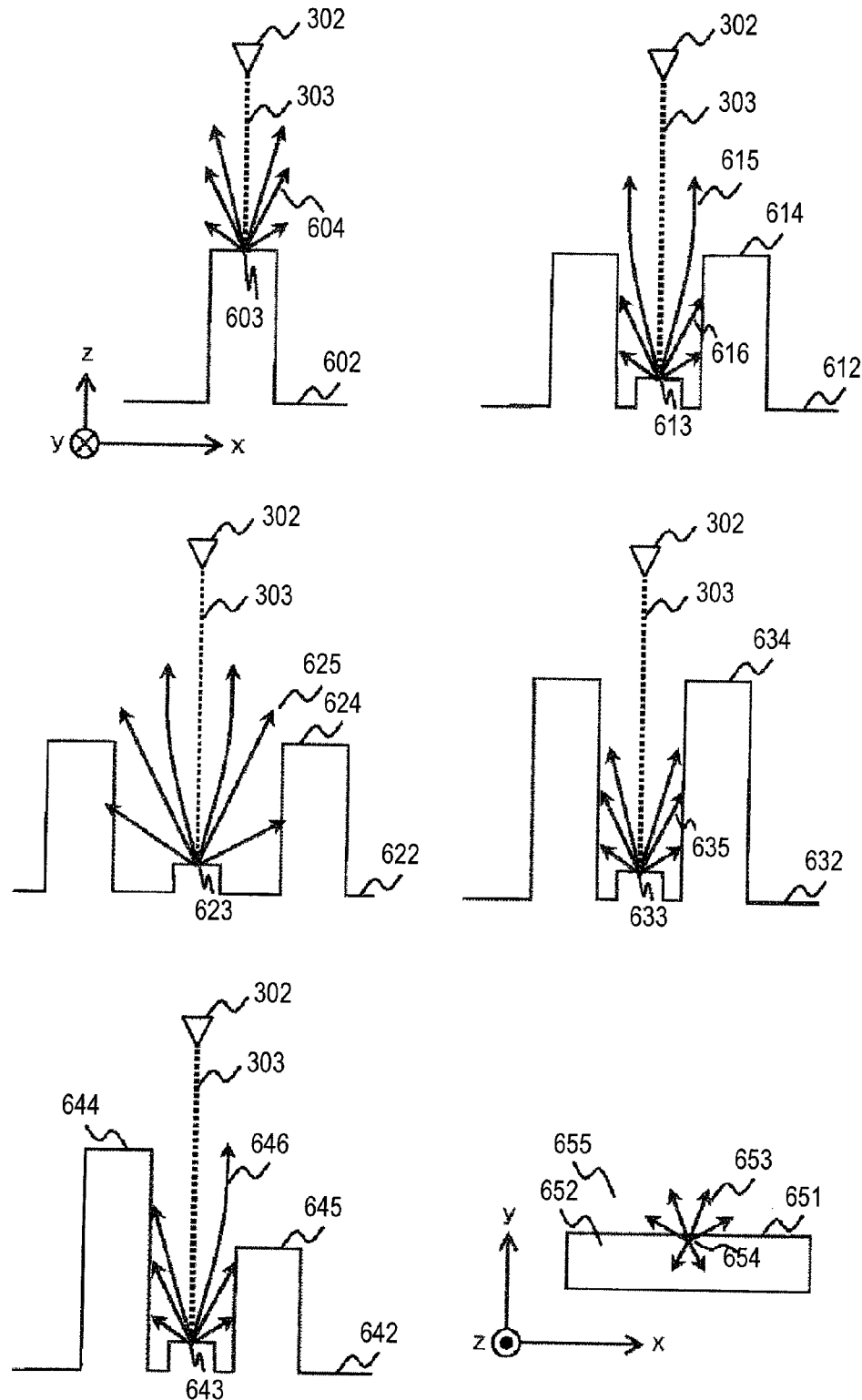
FIG. 6 is a schematic diagram showing the relationship between the shape of the sample and the detected amount of particles emitted from the sample.

FIG. 6 is a schematic diagram showing the relationship between the shape of the sample and the detected amount of particles emitted from the sample. Loci of particles emitted from each sample (602, 612, 622, 632, 642, 652) when the sample is irradiated with the charged particle beam 303 from the charged particle gun 302 are indicated by arrows. The samples are assumed to have the same electrical properties and material properties for the simplicity of the explanation. In each example, six arrows extending from the charged particle beam irradiation position are shown. The ratio of particles that can be detected by the detector decreases with the increase in the number of arrows colliding with the sample.

In the example of the sample 602, the charged particle beam irradiates a position 603 that is high in the sample, and thus particles emitted from the sample rarely collide with the sample again as indicated by arrows 604. Therefore, a large number of particles can be detected.

In the example of the sample 612, a part 614 around the irradiation position 613 of the charged particle beam is higher than the irradiation position 613, and thus part of the particles emitted from the sample collide with the sample and are absorbed as indicated by arrows 616. Therefore, the definition of the captured image corresponding to the position 613 is low. Incidentally, curved arrows like arrows 615 indicate that the loci of the particles draw curved lines like the arrows. For example, in cases where the particles have electrical charges, the loci of the particles can be bent like the arrows and more particles can be detected by setting an appropriate electric field above the sample.

In the example of the sample 622, a part 624 around the charged particle beam irradiation position 623 is higher than the irradiation position 623. While the level difference between the part 624 and the irradiation position 623 equals that between the part 614 and the irradiation position 613, the part 624 of the sample 622 is relatively far from the position 623 in the X direction, and thus the number of particles colliding with the sample is smaller compared to the case of the sample 612 as indicated by arrows 625. Therefore, the definition of the captured image corresponding to the position 623 becomes higher compared to the position 613.

In the example of the sample 632, a part 634 around the charged particle beam irradiation position 633 is higher than the irradiation position 633 and the level difference between the part 634 and the irradiation position 633 is greater compared to the case of the sample 612. In this case, the number of particles colliding with the sample becomes larger compared to the case of the sample 612 as indicated by arrows 635. Therefore, the definition of the captured image corresponding to the position 633 becomes lower compared to the position 613.

In the example of the sample 642, parts 644 and 645 around the charged particle beam irradiation position 643 are higher than the irradiation position 643 but the heights of the parts 644 and 645 differ from each other. Specifically, the height of the part 644 equals that of the part 634 and the height of the part 645 equals that of the part 614. In this case, the number of particles colliding with the part 645 differs from the number of particles colliding with the part 644 as indicated by arrows 646. Consequently, the number of particles colliding with the sample becomes larger compared to the case of the sample 612 and smaller compared to the case of the sample 632. Therefore, the definition of the captured image corresponding to the position 643 becomes lower compared to the position 613 and higher compared to the position 633.

In the example of the sample 652, the charged particle beam irradiates a position 654 in the vicinity of the edge 651. The inside of the rectangle corresponds to a high part of the sample; the height is low outside the rectangle. In this case where the charged particle beam irradiates a position (a part of the sample) that is high and in the vicinity of the edge, more particles are emitted in the direction in which the distance from the irradiation position 654 to the edge is shorter as indicated by arrows 653.

By using the relationship between the shape of the sample and the detected amount of particles emitted from the sample like the one shown in FIG. 6, it is possible to estimate the definition in each area of the captured image from information on the shape of the sample.

Figure 7:
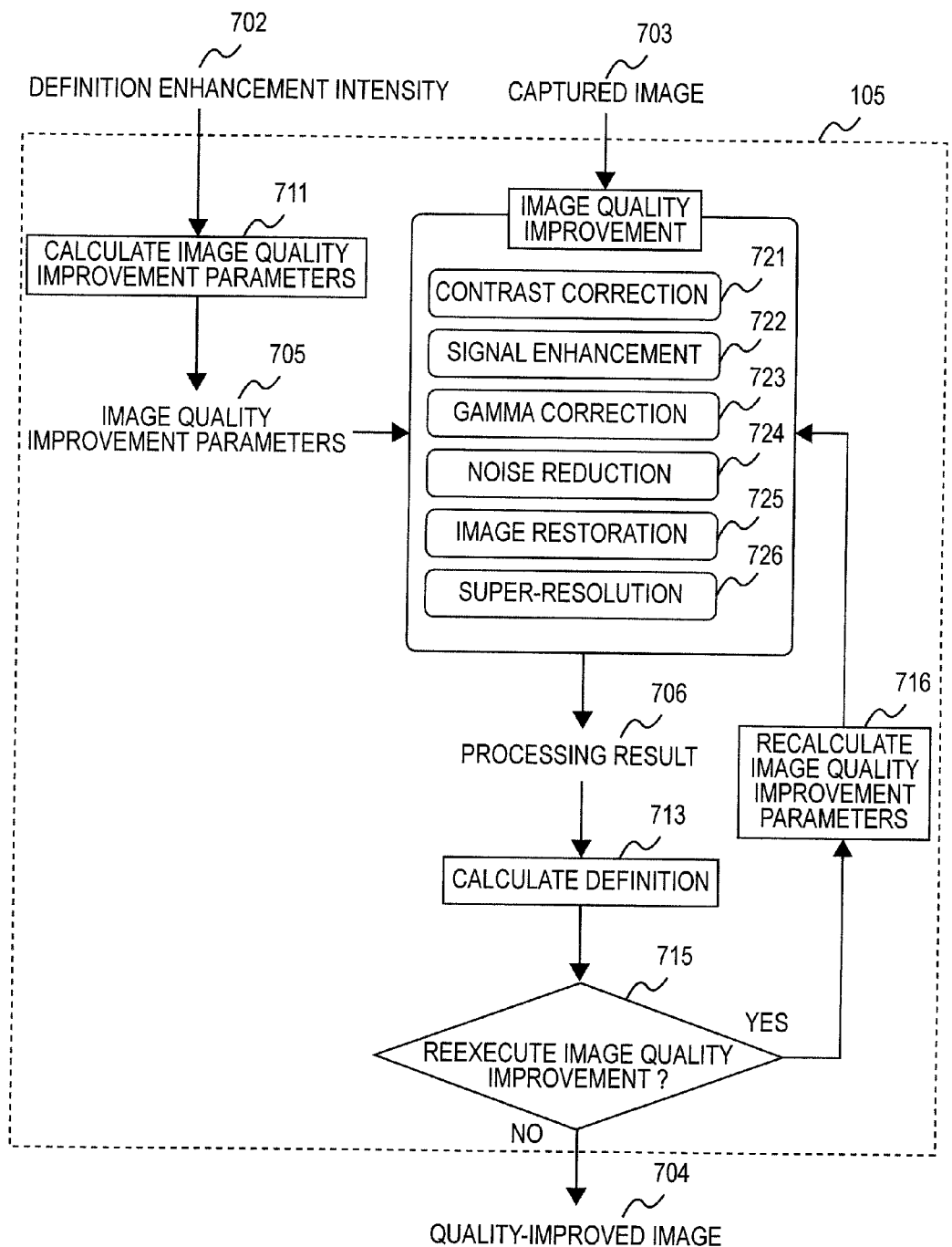
FIG. 7 is a schematic diagram showing an example of the image quality improvement process.

FIG. 7 is a schematic diagram showing an example of the image quality improvement process performed in the step 105. First, prescribed image quality improvement parameters 705 are calculated by use of the calculated definition enhancement intensity 702 (step 711). Subsequently, image quality improvement (step 712) is executed to the captured image 703 using the calculated image quality improvement parameters 705, by which a processing result 706 is acquired. The image quality improvement (step 712) is executed by performing one or more processes properly selected from a contrast correction process 721, a signal enhancement process 722, a gamma correction process 723, a noise reduction process 724, an image restoration process 725 and a super-resolution process 726. For example, when the contrast correction process 721 is executed, examples of the image quality improvement parameters 705 can include the variance of the brightness values or the target value itself of the quartile range of the brightness values, which are indexes of the definition, or other values calculated from the definition enhancement intensity (e.g., the average of the brightness values), and arbitrary combinations of these values. In step 713, the definition is calculated for the processing result 706. In the next step 715, whether the image quality improvement should be reexecuted or not is judged using the calculated definition. For example, the reexecution is judged to be necessary when the definition calculated in the step 713 is less than a prescribed value. When the reexecution is necessary, the image quality improvement in the step 712 is executed again by recalculating the image quality improvement parameters in step 716. When the reexecution is unnecessary, the processing result 706 is used as the quality-improved image 704. The steps 713, 715 and 716 may be left out when they are unnecessary. The image quality improvement process (step 105) explained above may be used in any one of the sequences shown in FIGS. 1, 2 and 4. According to this example, a quality-improved image having intended definition can be acquired by performing the image quality improvement process to the captured image.

Figure 8:
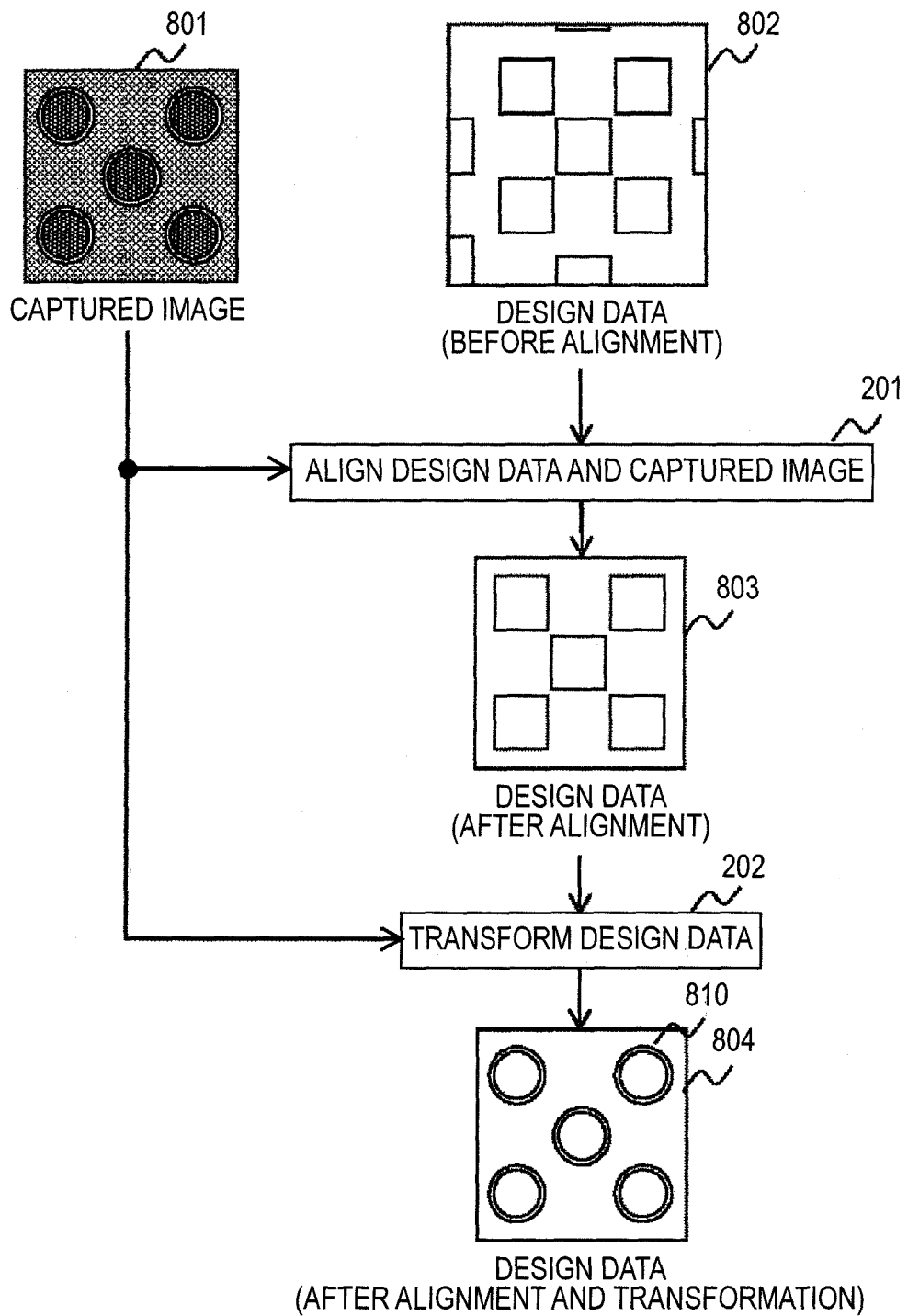
FIG. 8 is a schematic diagram showing an example of a process of aligning a captured image and the design data and a process of transforming the design data to make it fit with the captured image.

FIG. 8 is a schematic diagram showing an example of the process of aligning the captured image and the design data (step 201) and the process of transforming the design data to make it fit with the captured image (step 202). This explanation will be given by taking a captured image 801 corresponding to a hole pattern as an example. The design data 802 in FIG. 8 is design data (before alignment) corresponding to the captured image 801. The alignment (positional adjustment) is performed for the captured image 801 and the design data 802 in the step 201, by which design data 803 after alignment is acquired. The visual field of the design data 802 before alignment is secured larger than that of the captured image so that lack of necessary information will no occur in the design data corresponding to the captured image even after the alignment. As in this example, the pattern shapes in the design data 803 after the alignment can differ considerably from those in the captured image 801. Therefore, the design data 803 after the alignment is transformed using the captured image 801 in the step 202. A simulator such as a lithosimulator can be used for the transformation of the design data. In design data 810 after the alignment and the transformation, structure not existing in the original design data, such as white bands appearing at the edges of the holes, may be expressed.

Figure 13:
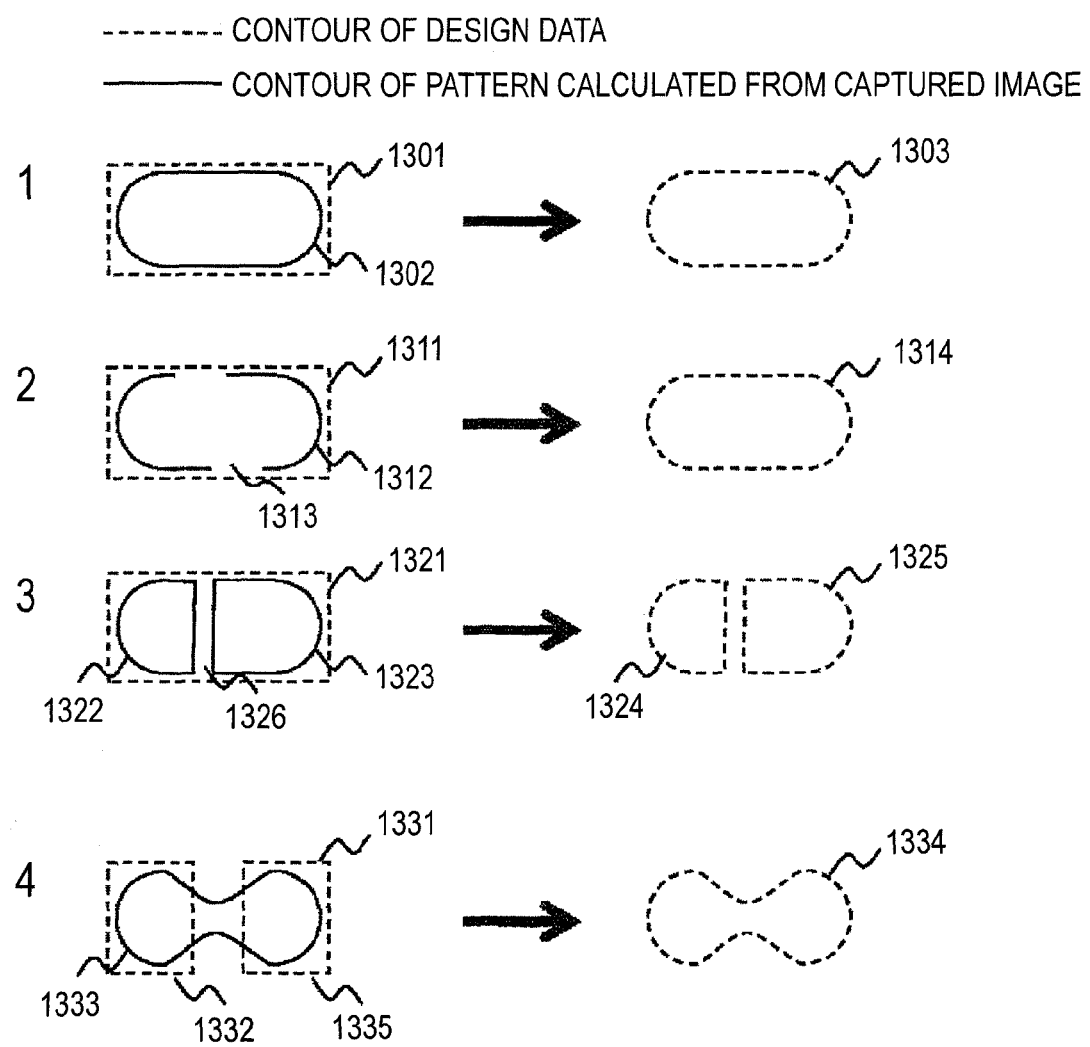
FIG. 13 is a schematic diagram showing an example of the process of transforming the design data to make it fit with the captured image.

FIG. 13 is a schematic diagram showing an example of the process of transforming the design data to make it fit with the captured image (step 202). In FIG. 13, contours of the patterns, defects, etc. calculated from the captured image (hereinafter referred to as "image contours") are indicated by solid lines while contours in the design data are indicated by dotted lines. The image contours can be calculated by executing an edge extraction process (e.g., differential filter) to the captured image, for example.

In the example (1), the image contour 1302 is rounder than the contour 1301 in the design data. In this case, the contour 1301 in the design data can be transformed into a shape similar to the image contour (like the contour 1303 after transformation) by gradually changing the contour 1301 in the design data.

In the example (2), the image contour 1312 should be identical with the aforementioned image contour 1302 but is partially disconnected (disconnection 1313) due to miscalculation in the image processing. In such calculation of an image contour from captured image by image processing, the calculated image contour is often disconnected as in this example depending on the calculation method. However, even when the image contour is disconnected to some extent, the contour 1311 in the design data can be transformed into a shape like the contour 1314 (after transformation) by bringing the contour 1311 close to the image contour 1312 while preventing the contour 1311 from being disconnected or becoming a complex curved line.

In the example (3), the image contour is separated into a first image contour 1322 and a second image contour 1323 due to disconnection in the actual pattern. In this case, the pattern is actually disconnected differently from the above example (2) in which the image contour is miscalculated. The disconnection at the position 1326 is evident also from the image contours 1322 and 1323. Therefore, the contour 1321 in the design data is desired to be transformed into shapes similar to the patterns 1322 and 1323. Since it can easily be judged from the image contours 1322 and 1323 that the image contours are made up of two closed curves, the contour 1321 in the design data can also be transformed into shapes like first and second contours 1324 and 1325 (after transformation) by changing the contour 1321 to make it expressed by two closed curves.

In the example (4), the contour 1331 in the design data is expressed by two closed curves (contour 1332, contour 1335), whereas the image contour 1333 is expressed by one closed curve due to a short circuit in the corresponding pattern. Also in this case, it can be judged that the image contour is made up of one closed curve. Thus, the contours in the design data can be transformed into a shape similar to the image contour (like the contour 1334 after transformation) by changing the contours in the design data to make them expressed by one closed curve.

By transforming the design data and bringing the contour(s) in the design data close to the correct image contour(s) (correctly calculated by the image processing) as in the above examples, the subsequent steps 203 (area partitioning) and 205 (calculation of the definition enhancement intensity) can be executed with high accuracy.

FIG. 27 is a schematic diagram showing an example of the process of transforming the design data to make it fit with the captured image in the case of the contour 1321 shown in FIG. 13. Similarly to FIG. 13, the image contours calculated from the captured image are indicated by solid lines while contours in the design data are indicated by dotted lines in FIG. 27.

First, a shape 2705 expressed by one closed curve is acquired by gradually changing the contour 1321 in the design data. As an example of a specific process, a certain number of points 2711 on the contour in the design data are moved to positions on the image contours in the vicinity of the points, respectively. In this example, the movement of the points is indicated by arrows 2712. After transforming the contour in the design data into the shape 2705, the difference between the transformed design data and the image contours is calculated. In this example, parts 2701 and 2702 of the image contours and parts 2703 and 2704 of the contour in the design data are acquired as the difference. When such (nonzero) difference exists, an analysis is conducted by checking the number of closed curves of the contour(s) in the design data and the number of closed curves of the image contour(s), for example. In this example, the number of closed curves of the contour(s) in the design data is one, whereas the number of closed curves of the image contour(s) is two. This indicates that the number of closed curves of the image contour(s) has increased due to disconnection, etc. Shapes like the first and second contours 1324 and 1325 after transformation can be acquired by increasing the number of closed curves of the contour(s) in the design data and thereafter gradually changing the contours in the design data. By such a process, the design data can be properly transformed to make it fit with the image contours.

Figure 14:
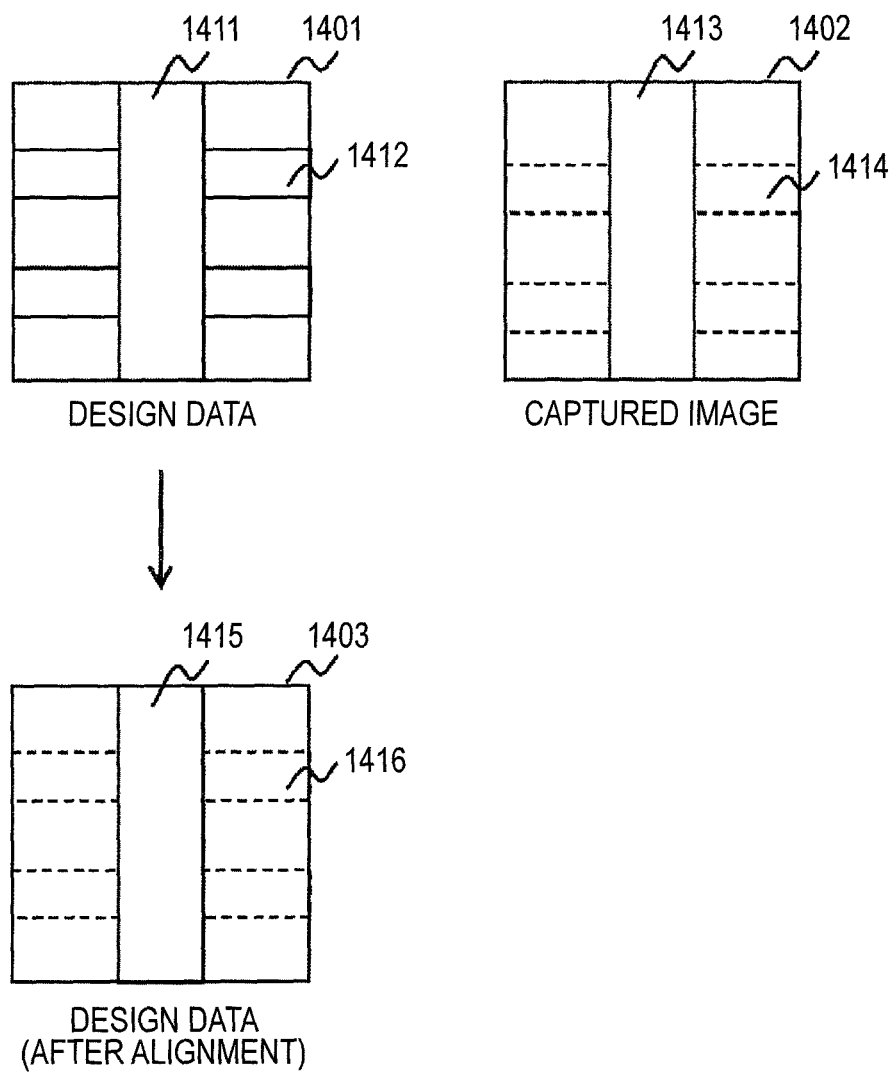
FIG. 14 is a schematic diagram showing an example of the process of aligning the captured image and the design data (step 201).

FIG. 14 is a schematic diagram showing an example of the process of aligning the captured image and the design data (step 201). The design data 1401 in FIG. 14 is design data corresponding to a captured image 1402. The design data 1401 includes an upper layer pattern 1411 and lower layer patterns. In the captured image 1402, signal components with high definition are indicated by solid lines while signal components with low definition are indicated by dotted lines. It is assumed in this example that the lower layer patterns 1414 are of low definition and hard to recognize by the image processing. In this case, the alignment of the design data and the captured image is possible in the crosswise direction by use of the upper layer pattern 1411; however, the alignment in the lengthwise direction is impossible since variations in the upper layer pattern 1411 in the lengthwise direction are extremely small. If the lower layer patterns 1414 are recognizable in the captured image, the alignment in the lengthwise direction is possible by aligning the lower layer patterns 1414 with the lower layer patterns 1412 in the design data. In this example, however, the alignment of the design data and the captured image in the lengthwise direction is difficult since the recognition of the lower layer patterns 1414 in the captured image is difficult.

Design data 1403 after the alignment in a case like this example is shown in FIG. 14, wherein dotted lines indicate patterns that could not be aligned. While the design data 1403 after the alignment indicates that the alignment in the lengthwise direction was impossible and the precise positions of the lower layer patterns could not be recognized, the fact that the recognition of the precise positions was impossible is implicitly indicating the existence of the lower layer patterns. Therefore, a process that is applicable even without determining the positions of the lower layer patterns (explained later) is executed, by which the definition can be improved properly.

Figure 26:
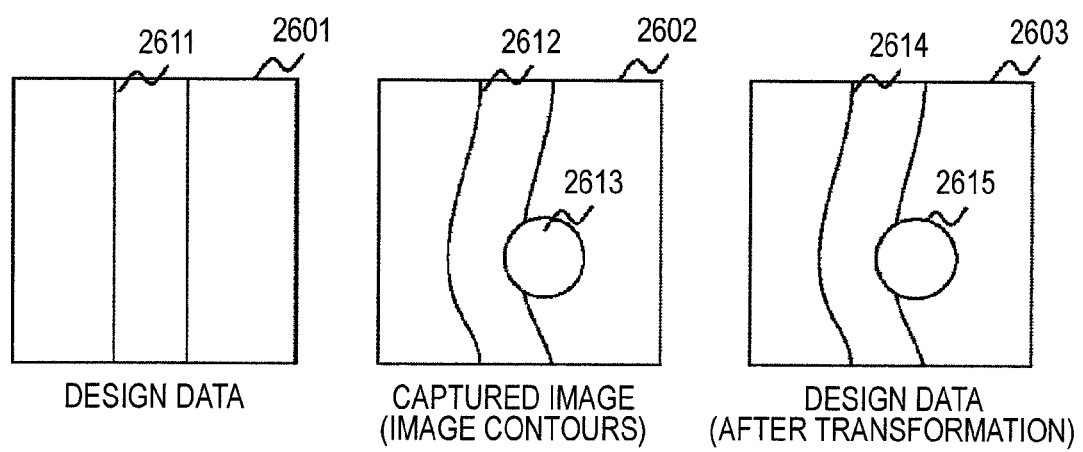
FIG. 26 is a schematic diagram showing an example of the process of transforming the design data to make it fit with the captured image.

FIG. 26 is a schematic diagram showing an example of the process of transforming the design data to make it fit with the captured image (step 202). The design data 2601 in FIG. 26 is an example of design data corresponding to a captured image 2602. In the captured image, the image contours are indicated by solid lines. From the comparison between the design data and the image contours in the captured image, it is apparent that a contour 2611 in the design data corresponds to an image contour 2612. The contour 2611 in the design data can be brought close to the shape of the image contour 2612 by gradually changing the contour 2611. The captured image 2602 in this example further includes an image contour of a foreign material 2613 which is not included in the design data. The image contour of the foreign material 2613 can be extracted by, for example, bringing the contour 2611 in the design data close to the corresponding image contour (by changing the contour 2611) and thereafter comparing the contours in the design data after the transformation with the image contours. Therefore, it is also possible to add information on the contour 2615 of the foreign material 2613, not included in the design data but included in the captured image, to the design data after the transformation.

FIG. 9 is a schematic diagram showing an example of a method of the area partitioning and a method of calculating the definition enhancement intensity. The design data 901 in FIG. 9 is design data corresponding to a captured image 902. In the captured image 902, upper layer patterns 911 and lower layer patterns 912 have been captured. Dotted lines in the captured image 902 indicate low visibility. Multilayer patterns generally have a problem of low visibility of lower layer patterns since it is difficult to detect, by a required amount, particles emitted from the lower layer patterns due to collision with an upper layer pattern, etc.

The diagram 903 in FIG. 9 shows an example of local areas acquired by the area partitioning, wherein the whole image has been partitioned into five local areas (local area a 913, local area b 914, local area c 915, local area d 916 and local area e 917) as upper layer patterns and the other areas. The area partitioning can be performed in this way by use of the information included in the design data 901 or information from the captured image 902.

The diagram 904 in FIG. 9 shows an example of the definition enhancement intensity calculated for each local area in the diagram 903. In the example of the diagram 904, areas in which the definition enhancement intensity equals 0 are filled in with white and areas having sufficiently high values of the definition enhancement intensity are filled in with hatching. In this example, definition enhancement intensity 0 is set to areas 918 corresponding to the upper layer patterns and sufficiently high definition enhancement intensity is set to areas 919 other than the upper layer patterns in order to improve the visibility of the lower layer patterns. This example is applicable also to cases like the example of FIG. 14 (where the precise positions of the lower layer patterns can not be recognized) since the definition enhancement intensity can be calculated in this example without the need of specifying the positions of the lower layer patterns.

The diagram 905 in FIG. 9 shows another example of local areas acquired by the area partitioning (executed differently from the diagram 903). In this example, the whole image has been partitioned into small-sized local areas. The area partitioning can also be performed independently of the information from the captured image or the design data as in this example.

The diagram 906 in FIG. 9 shows an example of the definition enhancement intensity calculated for each local area in the diagram 905, wherein the result of the calculation is expressed by the same filling method as in the diagram 904. In this example, the definition enhancement intensity is set high in edge parts 920 of the lower layer patterns.

The visibility of the lower layer patterns can be improved by setting the definition enhancement intensity as above. Incidentally, the definition enhancement intensity can also take on negative values. When the definition enhancement intensity is positive, the image quality improvement process is performed so that the definition in the quality-improved image becomes higher than the present definition. When the definition enhancement intensity is negative, the image quality improvement process is performed so that the definition in the quality-improved image becomes lower than the present definition.

FIG. 10 is a schematic diagram showing an example of the calculation of the definition enhancement intensity using the sample height information included in the design data. Height information 1002 corresponding to design data 1001 is plotted, wherein the Z-axis represents the height direction. In this example, the design data includes not only two-dimensional information 1001 but also the height information 1002. When only the two-dimensional information 1001 in the design data is used, patterns 1011a and 1012a appear to be equivalent upper layer patterns. However, the patterns differ in the height; the pattern 1012a is higher than the pattern 1011a as indicated by height information 1015a and 1016a. By using the height information, it is found that the patterns 1011a and 1011b are of the same height and the patterns 1012a and 1012b are of the same height. The heights 1015a, 1015b, 1016a and 1016b in the height information 1002 correspond to the patterns 1011a, 1011b, 1012a and 1012b in the two-dimensional information 1001, respectively. The lower layer patterns are of a uniform height in this example. Since the patterns 1012a and 1012b are both high, the detection of particles emitted from the area 1030 surrounded by the patterns 1012a and 1012b is especially difficult.

The graph 1003 indicates the detected amount of particles emitted from the sample (hereinafter referred to as a "particle count"). The positions 1021, 1022 and 1023 correspond to lower layer patterns. The particle count from the position 1023 is lower than that from the position 1021. This difference in the particle count can be explained by the difference in the heights of upper layer patterns on both sides of each position corresponding to each particle count. The upper layer patterns 1016a and 1016b on both sides of the position 1023 are higher than the upper layer patterns 1015a and 1015b on both sides of the position 1021, and thus particles emitted from the position 1023 tend more to collide with the patterns on both sides, resulting in the lower particle count. The particle count from the position 1022 is lower than that from the position 1021 and higher than that from the position 1023. This phenomenon, similar to that explained referring to FIG. 6, is easily understandable from the fact that the patterns on both sides of the position 1022 are the patterns 1015b and 1016a.

The graph 1004 indicates an example of the definition enhancement intensity. Since the particle counts shown in the graph 1003 can be estimated from the height information included in the design data, remarkable visibility improvement can be made for areas having relatively low visibility by setting the definition enhancement intensity higher for parts (positions) corresponding to lower particle counts.

Figure 11:
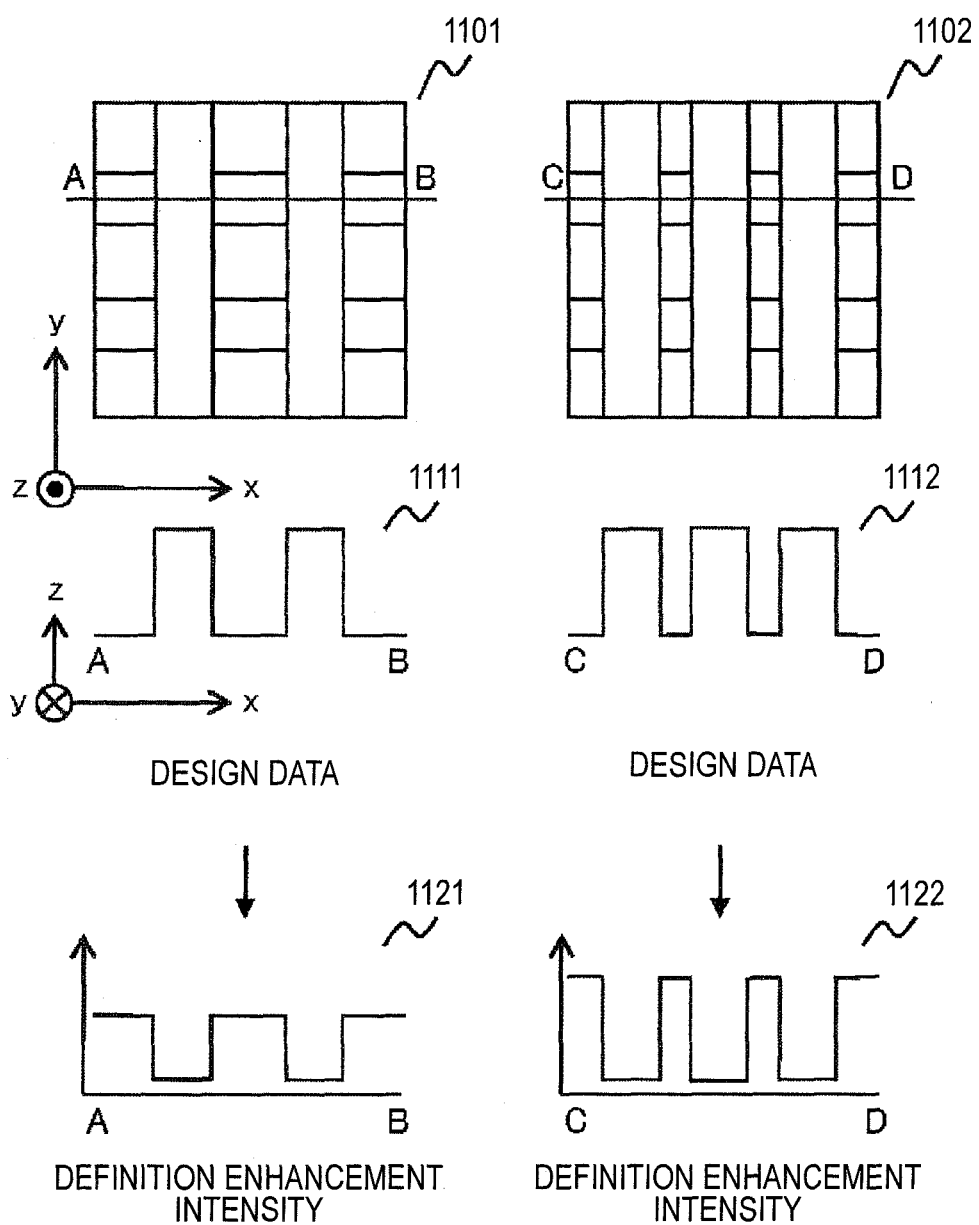
FIG. 11 is a schematic diagram showing an example of the calculation of the definition enhancement intensity for images differing in the aspect ratio.

FIG. 11 is a schematic diagram showing an example of the calculation of the definition enhancement intensity for images differing in the aspect ratio. The design data 1101 and 1102 shown in FIG. 11 are examples of design data corresponding to samples at different positions in the same process. Two pieces of height information (included in the design data) corresponding to the design data 1101 and 1102, respectively, are shown as height information 1111 and 1112. While the heights of the upper layer patterns and the lower layer patterns are identical between the design data 1101 and 1102, the upper layer patterns in the design data 1102 are more densely wired compared to those in the design data 1101.

Even when the pattern height information is identical as in this case, with the increase in the wiring density of the upper layer patterns, the particles emitted from the lower layer patterns tend more to collide with the upper layer patterns and the detection of the particles becomes more and more difficult. Thus, the visibility of the lower layer patterns in the captured image corresponding to the design data 1102 is generally lower than that in the captured image corresponding to the design data 1101. By use of information included in the design data, the denser pattern wiring in the design data 1102 compared to the design data 1101 can easily be recognized and the lower definition of the lower layer patterns in the captured image corresponding to the design data 1102 can be expected. In this example, the definition enhancement intensity is calculated using not only the level difference between the upper layer patterns and the lower layer patterns but also the density of the patterns or information on how close the upper layer patterns are. Examples of the definition enhancement intensity corresponding to the design data 1101 and 1102 are shown as definition enhancement intensity 1121 and 1122, respectively. By such a process, the definition enhancement intensity can be set high for design data that is expected to lead to low definition (e.g., the design data 1102).

Figure 15:
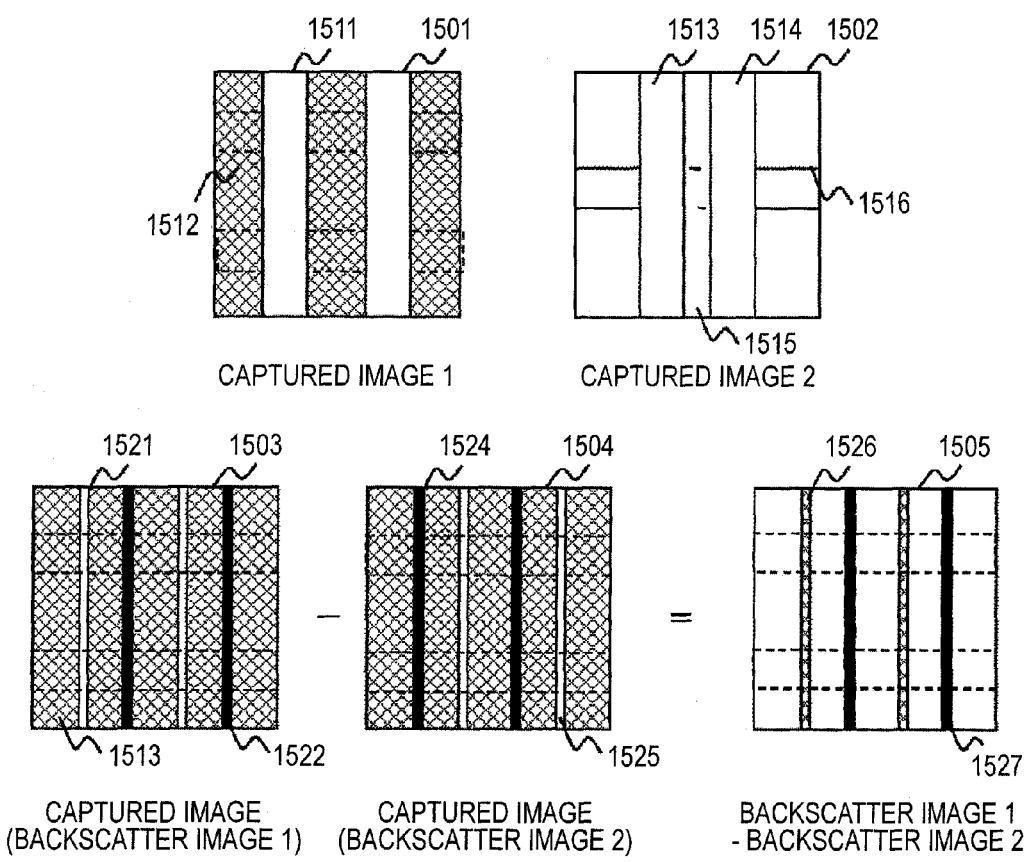
FIG. 15 is a schematic diagram showing an example of the estimation of the sample height information from the captured image.

FIG. 15 is a schematic diagram showing an example of the estimation of the sample height information from the captured image.

In the example of the captured image 1501, areas 1511 having high brightness values are filled in with white and areas 1512 having low brightness values are filled in with hatching. The brightness value tends to be low in areas of low in height since particles emitted from the sample (low areas) are detected with low probability. Therefore, the sample height information can be estimated by regarding areas having low brightness values as low areas in height and regarding areas having high brightness values as high areas in height. The sample height information can either be concrete values (e.g., 200 nm from a prescribed reference position) or information just indicating relative height relationship (e.g., "high" or "low"). Information indicating upper/lower layer relationship in a multilayer is also a type of the height information.

In the example of the captured image 1502, edges of patterns are expressed by black line segments. The captured image 1502 includes upper layer patterns 1513 and 1514 and a lower layer pattern 1516. In an intermediate area 1515 between the upper layer patterns 1513 and 1514 and the lower layer pattern 1516, the visibility of the lower layer pattern is low and the edges are hard to detect. However, by paying attention to the positional relationship among the line segments representing the edges of patterns, it is possible to estimate, from the captured image 1502 alone, that there exist the upper layer patterns 1513 and 1514 in the lengthwise direction and there exists the lower layer pattern 1516 in the crosswise direction beneath the upper layer patterns 1513 and 1514. Thus, it is possible to estimate that the area 1515 is lower than the upper layer patterns 1513 and 1514 by means of image processing. As above, the relative height relationship can be estimated by using the positional relationship among the line segments representing the edges of patterns.

The captured images 1503 and 1504 in FIG. 15 are other examples. The captured images 1503 and 1504 are two images acquired by irradiating the same part of a sample with charged particles and detecting backscattered particle with two backscattered particle detectors. In the captured images 1503 and 1504, areas 1521 having high brightness values are filled in with white, areas 1522 having low brightness values are filled in with black, and areas 1523 having intermediate brightness values are filled in with hatching. In each of these captured images, two patterns in the lengthwise direction have been captured. Each of the backscattered particle detectors is arranged so that backscatter particles emitted leftward/rightward with respect to the captured image can be detected more. It is well known that information on concavities and convexities of the sample can be obtained by calculating the difference between the captured images 1503 and 1504 acquired as above. In the difference image 1505, areas in which the value (difference) is approximately 0 are filled in with white. For the other areas, areas having positive values are filled in with hatching and areas having negative values are filled in with black. Each area 1526 filled in with hatching indicates that the sample height in an adjoining area to the right of the considered area (rightward adjoining area) is higher than that in an adjoining area to the left of the considered area (leftward adjoining area). Each area 1527 filled in with black indicates that the sample height in the rightward adjoining area is lower than that in the leftward adjoining area. By using this type of information, the relative height relationship can be acquired by means of image processing.

Once the height information is estimated, it is possible to judge, for example, that local areas that are relatively high compared to surrounding areas do not need the definition enhancement since particles emitted from such local areas can easily be detected. As described above, the calculation of the definition enhancement intensity can be executed more properly by use of the height information. Incidentally, the image used for the estimation of the height information and the image for which the calculation of the definition enhancement intensity and the image quality improvement process are performed can be different from each other. For example, it is possible in the example of the captured images 1503 and 1504 to estimate the height information using these images 1503 and 1504 and thereafter perform the image quality improvement process to another image (acquired by another detector) using the estimated height information.

Figure 16:
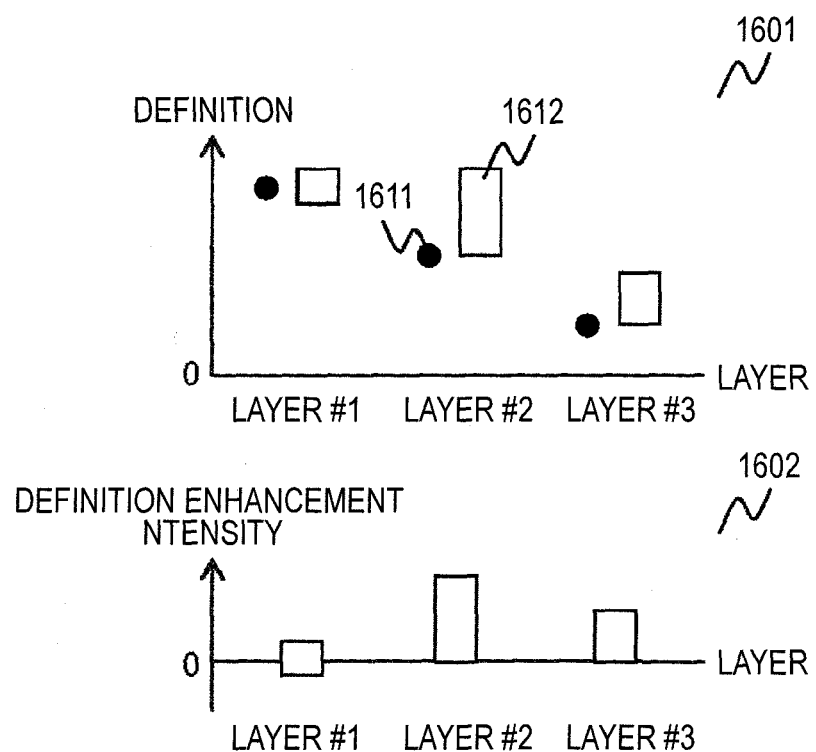
FIG. 16 is a schematic diagram showing an example of a method for setting constraint conditions on the definition enhancement intensity using present definition calculated from the captured image.

FIG. 16 is a schematic diagram showing an example of a method for setting constraint conditions on the definition enhancement intensity using the present definition calculated from the captured image. The graph 1601 in FIG. 16 shows the relationship between the constraint conditions and the present definition of each layer in a captured image acquired by capturing a three-layer pattern. In the graph 1601, black circles 1611 represent the present definition and white rectangles 1612 represent the constraint conditions. In each white rectangle, the top line segment represents the upper limit of the definition required of the quality-improved image (hereinafter referred to as "target definition") and the bottom line segment represents the lower limit of the target definition.

In this example, the definition decreases with the increase in the layer number assigned from the top layer (uppermost layer). Since the definition of the second layer from the top and that of the third layer are low, the definition enhancement intensity has to be set high for these layers. However, it is not necessarily true that higher definition enhancement intensity is better. In order not to deteriorate the image quality of the entire image, it is generally necessary to set the definition of a lower layer (relatively lower layer) lower than that of an upper layer (relatively higher layer) in the quality-improved image. Further, excessively high definition of an area can deteriorate the image quality of low-definition areas since the area with excessively high definition stands out too much. Furthermore, the image can become unnatural as a whole if the relative magnitude relationship (high/low relationship) regarding the definition is broken by the image quality improvement process. When the definition in the quality-improved image is too high relative to the present definition, side effects such as amplified noise and appearance of artificial patterns can be caused.

Therefore, in this example, constraint conditions regarding the definition are set as needed in order to suppress these side effects. The constraint conditions can be set, for example, so that the definition of each layer will not exceed that of an upper layer (higher layer), the definition will not be excessively high, and the definition will not be too high relative to the present definition as mentioned above. By setting such constraint conditions regarding the definition, the above side effects can be suppressed.

The graph 1602 in FIG. 16 shows an example of the constraint conditions on the definition enhancement intensity. The constraint conditions can be determined by subtracting the present definition from the constraint conditions regarding the definition in the quality-improved image, for example. While this explanation has been given by taking a three-layer pattern as an example, it is of course possible to set the constraint conditions similarly for other multiple-layer patterns.

Figure 17:
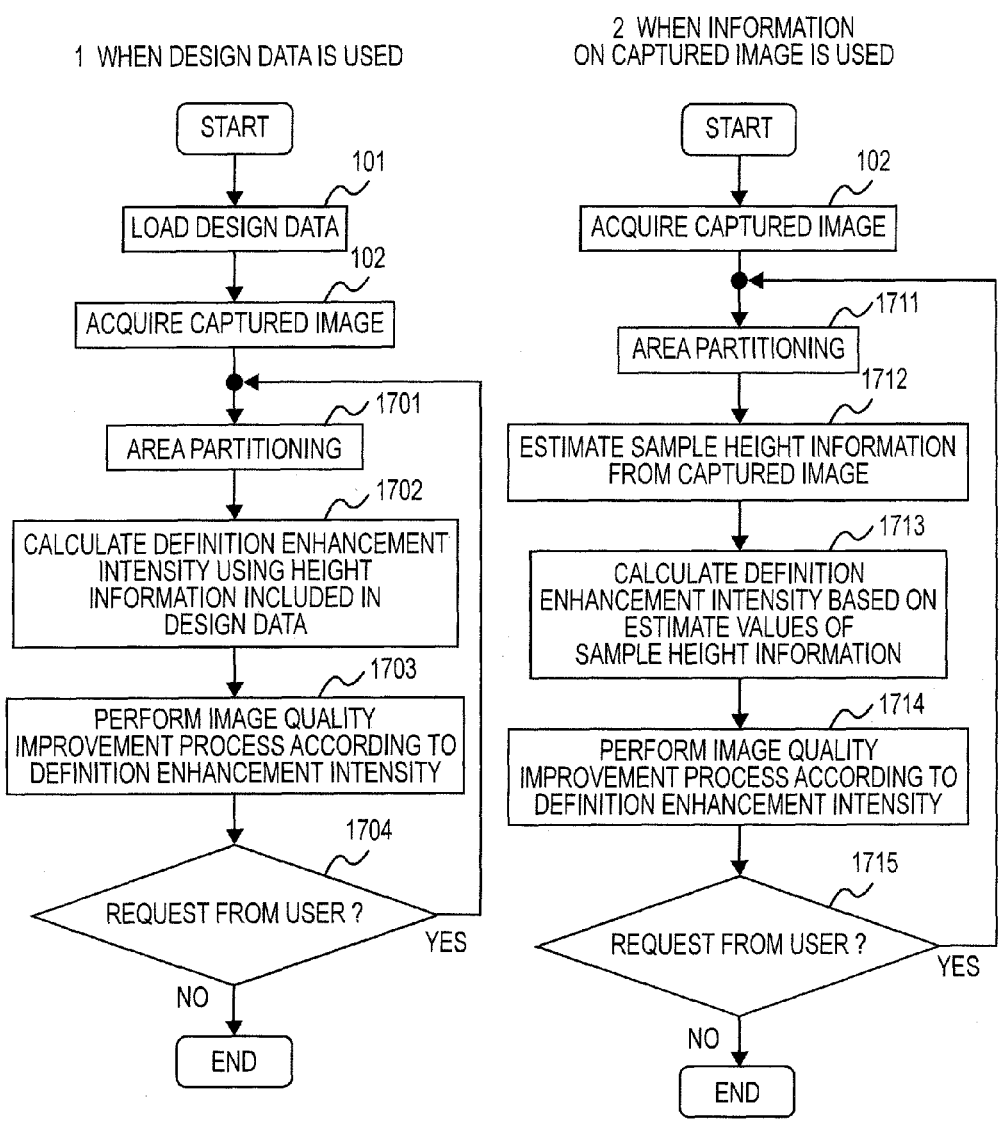
FIG. 17 is a flow chart showing examples of a sequence for prompting the user to input information regarding areas for which the user wants to specify the definition enhancement intensity or information regarding the definition enhancement intensity and calculating the definition enhancement intensity based on the information specified by the user.

FIG. 17 is a flow chart showing examples of a sequence for prompting the user to input information regarding areas for which the user wants to specify the definition enhancement intensity or information regarding the definition enhancement intensity and calculating the definition enhancement intensity based on the information specified by the user.

FIG. 17(1) shows an example of the sequence when the design data is used. The steps 101 and 102 in FIG. 17(1) are equivalent to those in FIG. 1. Subsequently, the area partitioning is executed to the captured image (step 1701). For each local area of the captured image acquired by the area partitioning, the definition enhancement intensity is calculated using the height information included in the design data (step 1702). Subsequently, the image quality improvement process is performed according to the definition enhancement intensity, by which the quality-improved image is acquired (step 1703). Then, a request from the user regarding areas for which the user wants to specify the definition enhancement intensity or regarding the definition enhancement intensity is inputted (step 1704). If there is a request from the user, the steps 1701-1703 are executed again according to the request. Thereafter, the steps 1701-1704 are repeated until the user inputs no request in the step 1704.

FIG. 17(2) shows an example of the sequence when the definition enhancement intensity is calculated using information from the captured image. The step 102 in FIG. 17(2) is equivalent to that in FIG. 1. Similarly to the case of FIG. 4, a step of loading the design data may also be executed in preparation for cases where the design data is used together. Subsequently, the area partitioning is executed to the captured image (step 1711). Subsequently, the sample height information is estimated from the captured image (step 1712). For each local area of the captured image acquired by the area partitioning, the definition enhancement intensity is calculated using the sample height information (step 1713). Subsequently, the image quality improvement process is performed according to the definition enhancement intensity, by which the quality-improved image is acquired (step 1714). Then, a request from the user regarding areas for which the user wants to specify the definition enhancement intensity or regarding the definition enhancement intensity is inputted (step 1715). If there is a request from the user, the steps 1711-1714 are executed again according to the request. Thereafter, the steps 1711-1715 are repeated until the user inputs no request in the step 1715.

Figure 18:
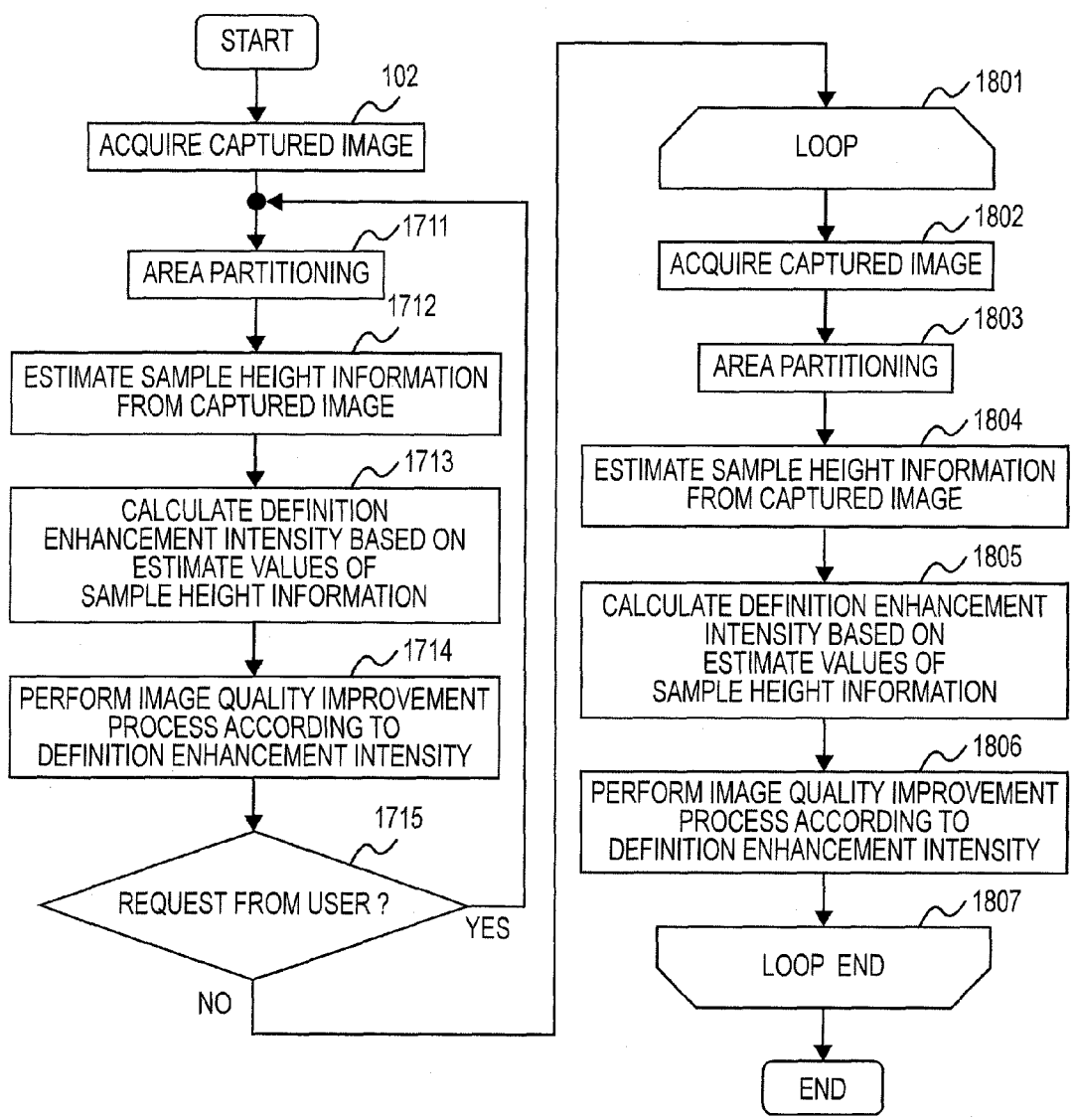
FIG. 18 is a flow chart showing an example of a sequence for prompting the user to input information regarding areas for which the user wants to specify the definition enhancement intensity or information regarding the definition enhancement intensity and calculating the definition enhancement intensity based on the information specified by the user.

FIG. 18 is a flow chart showing another example of a sequence for prompting the user to input information regarding areas for which the user wants to specify the definition enhancement intensity or information regarding the definition enhancement intensity and calculating the definition enhancement intensity based on the information specified by the user. In this sequence, images of multiple parts of the sample are captured. The steps 102-1715 in FIG. 18 are equivalent to those in FIG. 17. By these steps, an output image for a captured image acquired first is generated. Thereafter, output images for remaining captured images are acquired by repeating steps 1801-1807 as a loop. In the loop, a captured image is acquired in step 1802 and the area partitioning is executed in step 1803. The sample height information is estimated from the captured image in step 1804, the definition enhancement intensity is calculated based on the estimate values of the sample height information in step 1805, and the image quality improvement process is performed according to the definition enhancement intensity in step 1806.

In cases where images of multiple parts of samples in the same process are captured, the properties of the captured images of the multiple parts are similar to one another and thus it is unnecessary to load a request from the user for each part. Thus, just prompting the user (to input a request) once at the beginning as in this sequence is sufficient. This sequence relieves the user of the need of inputting the request (regarding areas for which the user wants to specify the definition enhancement intensity or regarding the definition enhancement intensity) on each image capturing in cases where images of multiple parts of samples are captured. Since the user has only to input the request once at the beginning, the user's tasks necessary for adjusting the image quality of the output images can be reduced remarkably. Incidentally, a step for letting the user further input a request as needed may be added to the loop (steps 1801-1807).

Figure 19:
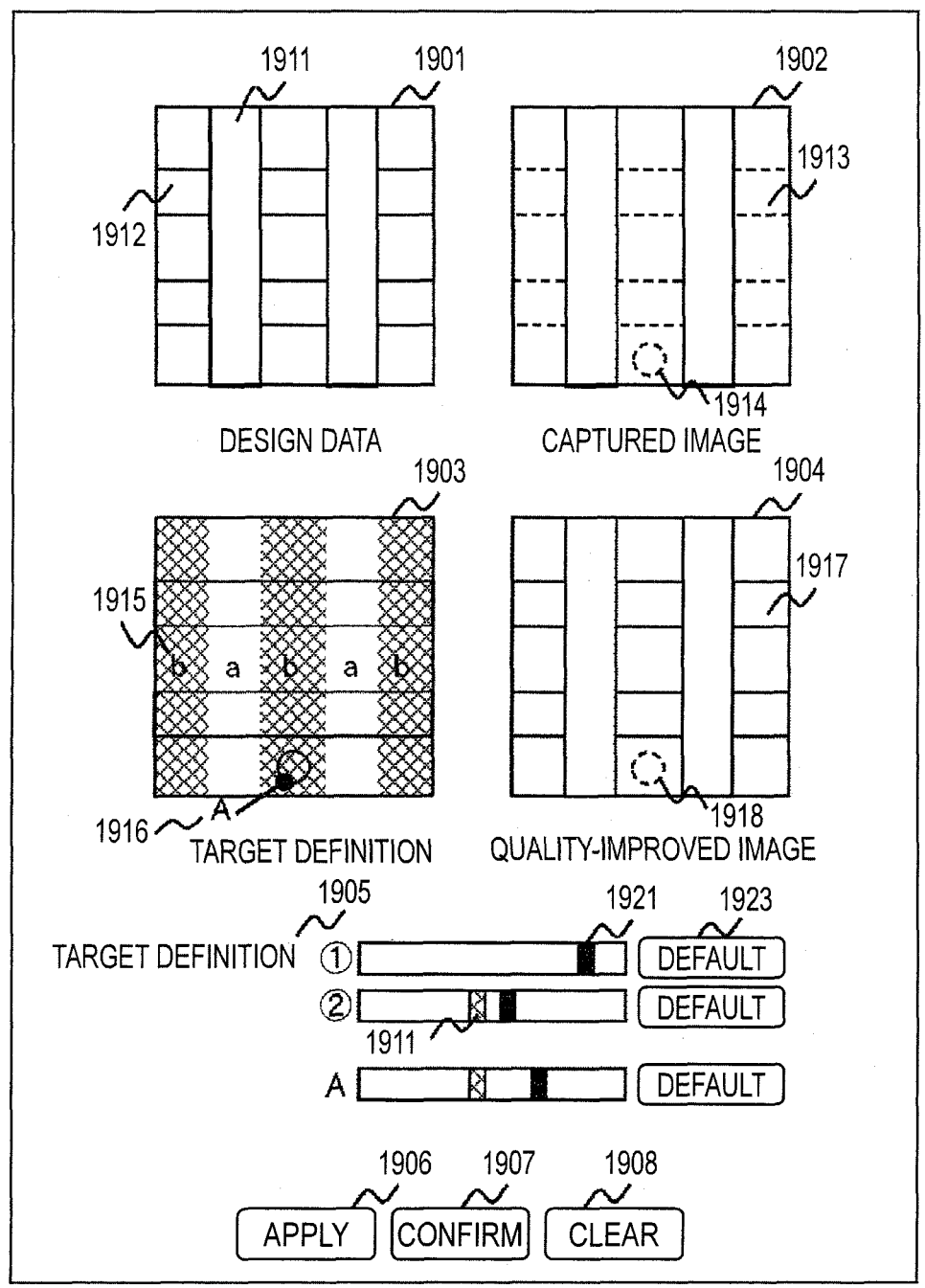
FIG. 19 is a schematic diagram showing an example of an interface for prompting the user to input information regarding areas for which the user wants to specify the definition enhancement intensity or information regarding the definition enhancement intensity.

FIG. 19 is a schematic diagram showing an example of an interface for prompting the user to input information regarding areas for which the user wants to specify the definition enhancement intensity or information regarding the definition enhancement intensity. Design data 1901, a captured image 1902, etc. have been properly displayed on the screen. In this example, an image of a part including upper layer patterns 1911 and lower layer patterns 1912 has been captured. When no design data is used, the displaying of the design data 1901 is left out. While signal components with high definition are indicated by solid lines and signal components with low definition are indicated by dotted lines in the captured image 1902, the expression of the captured image 1902 may be made in different ways (e.g., by using different colors). In this example, the lower layer patterns 1912 are of low definition and a defect 1914 has also been captured.

In a screen area 1903, default values of the target definition are displayed. In the target definition area 1903, areas filled in with white represent areas with high definition and areas filled in with hatching represent areas with lower definition compared to the areas filled in with black.

In a screen area 1904, a quality-improved image acquired by performing the image quality improvement process according to definition enhancement intensity calculated from the target definition 1903 is displayed. In the quality-improved image 1904, parts with high definition are indicated by solid lines and parts with low definition are indicated by dotted lines similarly to the captured image 1902. In this example of the quality-improved image 1904, the lower layer patterns 1917 are displayed with high definition, whereas the definition of the defect 1918 is insufficient.

In a screen area 1905, an interface for letting the user specify the target definition is displayed. Local areas for which the user wants to specify the target definition can be designated in the aforementioned target definition area 1903, for example. The user can specify the target definition separately for areas representing the upper layer patterns and the other areas (e.g., "areas a" and "areas b" 1915). The user can specify the target definition also for the area representing the defect (e.g., "areas A" 1916).

The interface 1905 for specifying the target definition can be implemented by scroll bars, for example. In this example, each mark 1921 represents the target definition specified by the user and each mark 1922 represents the default value of the target definition. When a "DEFAULT" button 1923 is clicked, the target definition 1921 specified by the user is returned to the default value 1922. The interface further includes an "APPLY" button 1906, a "CONFIRM" button 1907 and a "CLEAR" button. When the "APPLY" button 1906 is clicked, the image quality improvement process is performed using the target definition specified by the user. When the "CONFIRM" button 1907 is clicked, the user input is ended by employing the target definition currently specified by the user as the final target definition. When the "CLEAR" button is depressed, the inputs by the user are cleared to the initial state.

While an interface for inputting the target definition as information on the definition enhancement intensity has been shown in this example, other interfaces, such as an interface for specifying the definition enhancement intensity itself or other information on the definition enhancement intensity, may also be employed.

As above, the interface allowing the user to input the information (regarding areas for which the user wants to specify the definition enhancement intensity or input information regarding the definition enhancement intensity) for each image or for each process is employed and the definition enhancement intensity is calculated based on the input. Therefore, an image having appropriate definition in conformity with the user's intention can be outputted.

Figure 20:
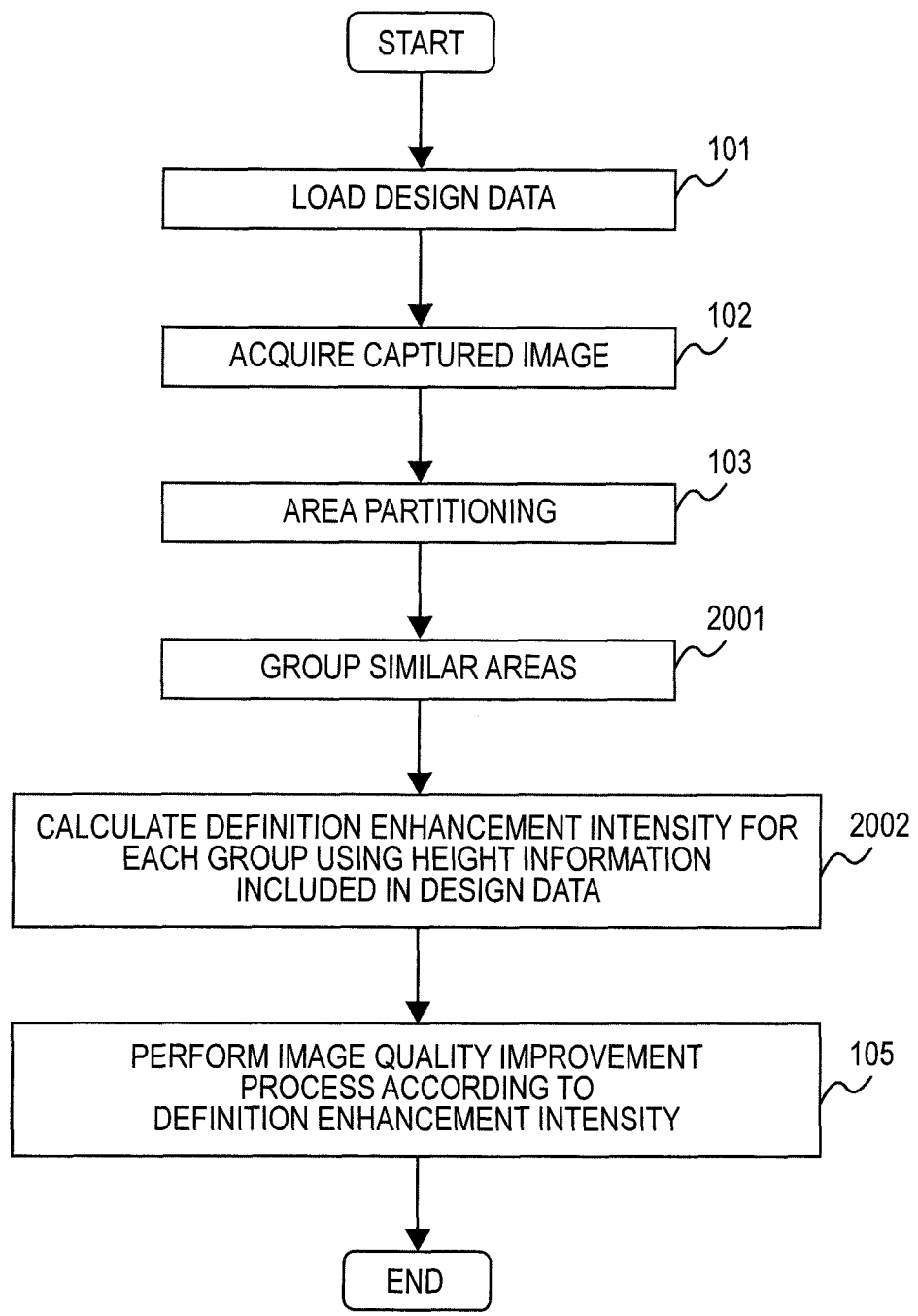
FIG. 20 is a flow chart showing an example of a sequence for grouping similar areas and assigning the same or close values of the definition enhancement intensity to areas belonging to the same group.

FIG. 20 is a flow chart showing an example of a sequence for grouping similar areas and assigning the same or close values of the definition enhancement intensity to areas belonging to the same group. The steps 101-103 in FIG. 20 are equivalent to those in FIG. 1. Subsequently, similar areas are grouped in step 2001. In step 2002, the definition enhancement intensity is calculated for each group using the height information included in the design data. In the final step 105, the image quality improvement process is performed according to the definition enhancement intensity. While the design data is used in this example, it is also possible to similarly conduct the grouping and assign the same or close values of the definition enhancement intensity to areas belonging to the same group even when estimated values of the height information are used instead of the design data.

Figure 21:
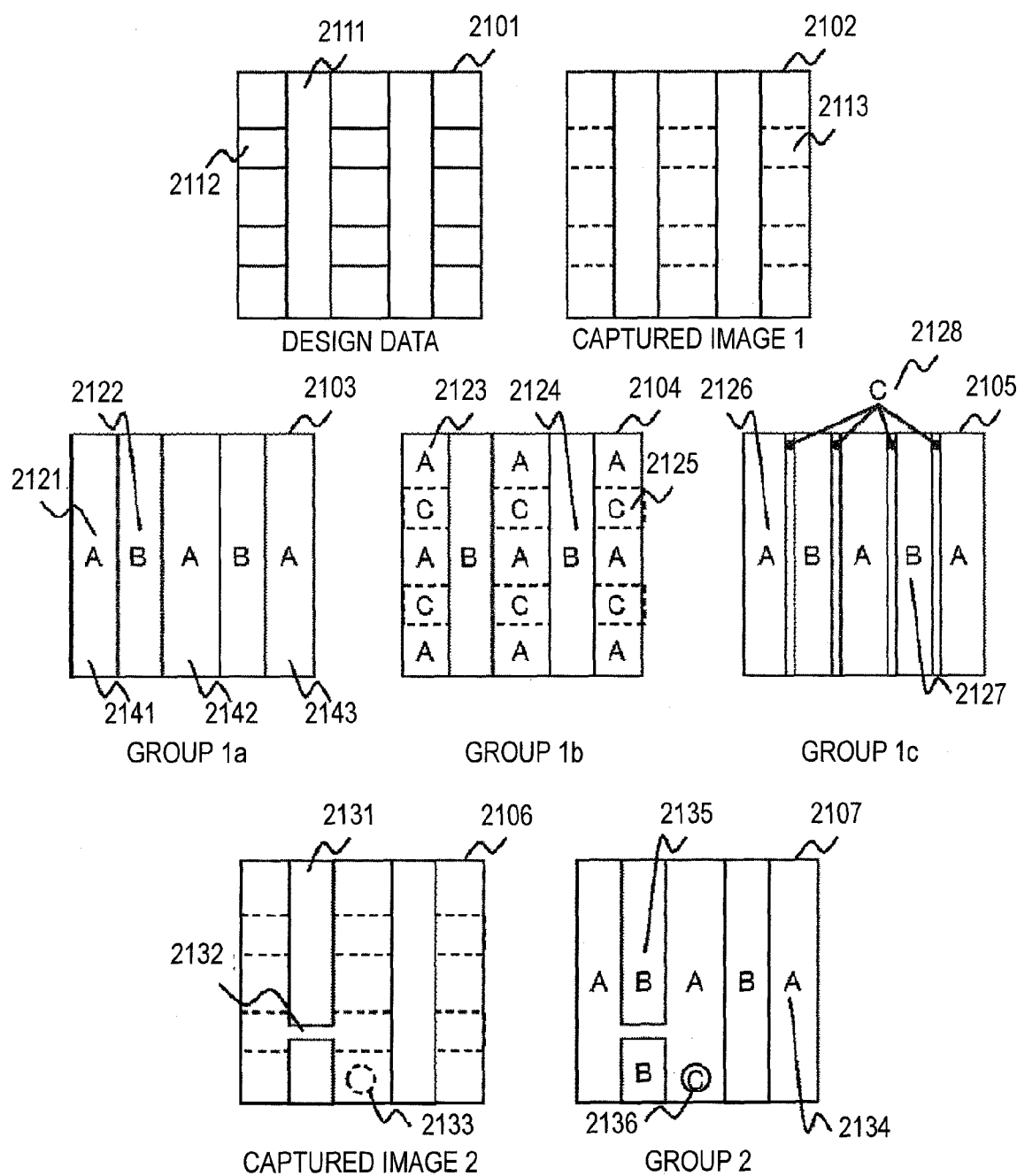
FIG. 21 is a schematic diagram showing an example of a method for the grouping of similar areas.

FIG. 21 is a schematic diagram showing an example of a method for the grouping of similar areas (step 2001 in FIG. 20). In FIG. 21, the image 2101 shows an example of the design data and the image 2102 shows an example of the captured image corresponding to the design data. In this example, upper layer patterns 2111 and lower layer patterns 2112 have been captured. In FIG. 21, signal components with high definition are indicated by solid lines and signal components with low definition are indicated by dotted lines. The lower layer patterns 2113 in the captured image 2102 are of low definition.

Three examples 2103-2105 of the result of the grouping of similar areas (step 2001 in FIG. 20) executed to the captured image 2102 are shown. In the example 2103 (group 1*a*), the areas are grouped into a group B 2122 representing the upper layer patterns and a group A 2121 representing the other areas. The area A (group A) groups three areas 2141, 2142 and 2143 which are spatially separate from one another. The areas 2141, 2142 and 2143 are similar to one another in the sense that each area includes a lower layer pattern. By executing this type of grouping, the image quality improvement process can be performed by setting uniformly high definition enhancement intensity to the group A, by which the definition of this group in the output image can be kept even.

In the example 2104 (group 1*b*), the areas are grouped into a group B 2124 representing the upper layer patterns, a group C 2125 representing the lower layer patterns, and a group A 2123 representing the other areas. It is possible, for example, to exclusively enhance the definition of the surfaces of the lower layer patterns by setting positive definition enhancement intensity exclusively to the group C.

It is also possible, as in the example 2105 (group 1*c*), to group the areas into a group B 2127 representing the upper layer patterns, a group C 2128 representing white band areas in the upper layer patterns, and a group A 2126 representing the other areas. By executing this type of grouping, it is possible, for example, to enhance the definition of the upper layer patterns except the white bands and the definition of the lower layer patterns while maintaining the definition of the white bands at the present level.

Another example of a captured image corresponding to the design data 2101 is shown as a captured image 2106. In this example, a disconnection 2132 in an upper layer pattern 2131 and a defect 2133 are displayed. An example of the result of the grouping executed to the captured image 2106 is shown as an image 2107. In this example, the areas are grouped into a group B 2135 representing the upper layer patterns, a group C 2136 representing a defect area, and a group A 2134 representing the other areas. The grouping shown in the image 2107 is easily possible since the existence of the pattern disconnection can be recognized by use of the design data 2101 and the captured image 2 (2106). While the design data is used in this example, similar grouping is possible also in the method recognizing areas using the captured image.

Figure 22:
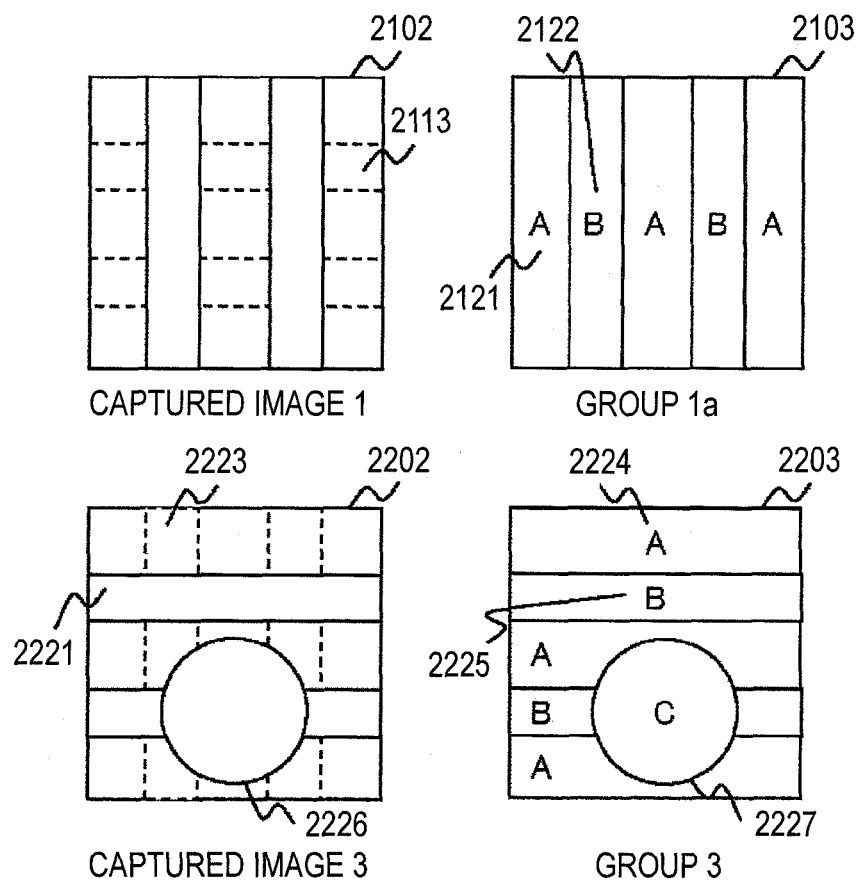
FIG. 22 is a schematic diagram showing an example of a method for the grouping of similar areas.

FIG. 22 is a schematic diagram showing another example of a method for the grouping of similar areas (step 2001 in FIG. 20). The captured image 1 2102 and the group 1*a* 2103 in FIG. 22 are identical with those in FIG. 21. Similarly to FIG. 21, signal components with high definition are indicated by solid lines and signal components with low definition are indicated by dotted lines in FIG. 22. The captured image 2202 shown below is an image acquired by capturing a different part of a sample in the same process as the captured image 2102. In the captured image 2202, upper layer patterns 2221 in the crosswise direction, lower layer patterns 2223 in the lengthwise direction and a large defect 2226 have been captured. The image 2203 to the right shows an example of the result of the grouping executed to the captured image 2202. In the image 2203 (group 3), the areas are grouped into a group B 2225 representing the upper layer patterns, a group C 2227 representing a defect area, and a group A 2224 representing the other areas.

Since the captured images 2102 and 2202 are images acquired by capturing samples of the same process, it is desirable in many cases that similar areas have close definition values in the output images. In this case, it is desirable to set the definition enhancement intensity so that the groups A in the image 2103 (group 1*a*) and the image 2203 (group 3) have definition values close to each other and the groups B in the image 2103 (group 1*a*) and the image 2203 (group 3) have definition values close to each other. In this example, the upper layer patterns and the lower layer patterns can be recognized by using the captured images 2102 and 2202, and prior information "in the same process" is also acquired. Therefore, it is possible to execute the grouping of similar areas in the same way for a plurality of captured images (e.g., the captured images 2102 and 2202) and set the definition enhancement intensity so that equivalent groups in the captured images have close definition values. While the grouping in this example is executed using information from the captured images only, similar grouping is also possible by use of the design data.

Figure 23:
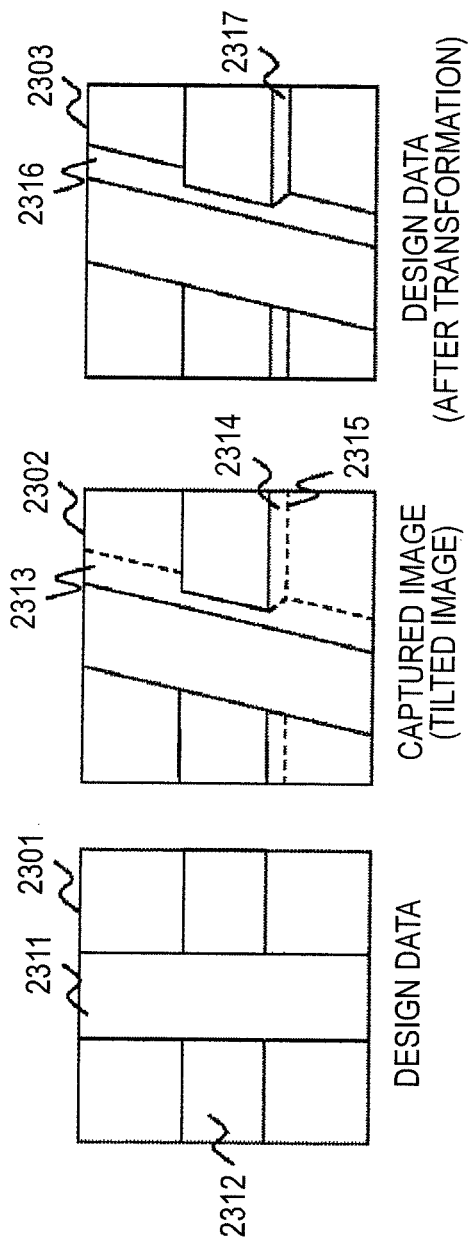
FIG. 23 is a schematic diagram showing an example of a method for transforming the design data for a captured image acquired by irradiating the sample with a charged particle beam in a direction not orthogonal to the sample.

FIG. 23 is a schematic diagram showing an example of a method for transforming the design data (step 202 in FIG. 2) for a captured image acquired by irradiating the sample with the charged particle beam in a direction not orthogonal to the sample (hereinafter referred to as a "tilted image"). The image 2301 shows an example of the design data, in which an upper layer pattern 2311 and a lower layer pattern 2312 are shown. The image 2302 shows an example of the tilted image corresponding to the design data 2301. In such a tilted image, a side wall 2313 of the upper layer pattern and a side wall 2314 of the lower layer pattern tend to be captured. In such cases, the shape of each pattern in the tilted image becomes more complex than in the design data and even a boundary 2315 between a pattern's side wall and the base is displayed, for example. In the tilted image 2302, signal components with high definition are indicated by solid lines and signal components with low definition are indicated by dotted lines.

Compared to images acquired by irradiating the sample with the charged particle beam in the orthogonal direction, the resolution tends to be deteriorated in tilted images since the diameter of the charged particle beam irradiating the sample can not be narrowed enough. Thus, achieving sufficient definition is sometimes impossible in a tilted image. When the definition enhancement intensity is calculated for a tilted image using the design data, it is difficult to directly compare the tilted image and the design data since the structures displayed in the images 2301 and 2302 have considerably different shapes. Therefore, the design data 2301 is transformed so as to bring it close to the captured image 2302. The image 2303 shown in FIG. 23 can be acquired by using appropriate information such as the angle between the sample and the irradiating charged particle beam and the height information included in the design data. Therefore, by using the tilted image 2302 and the transformed design data 2303, the calculation of the definition enhancement intensity can be conducted in the same ways as the aforementioned case where the captured image is not a tilted image.

Figure 24:
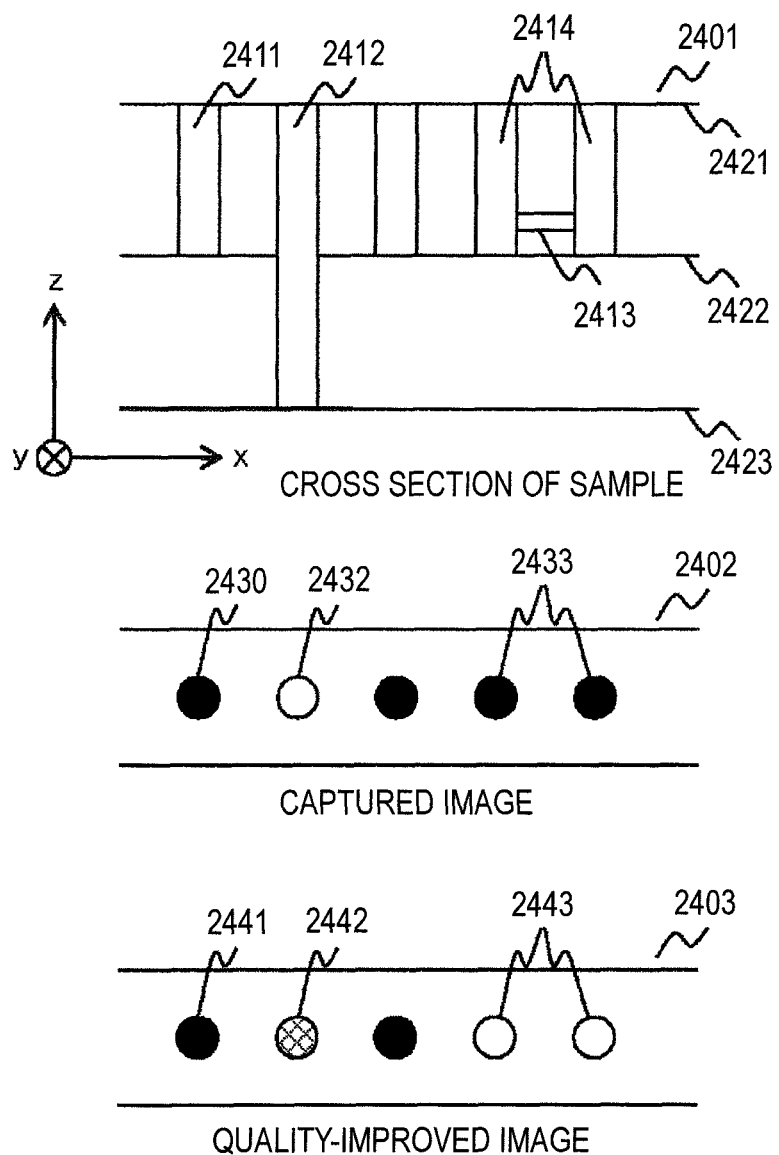
FIG. 24 is a schematic diagram showing an example of a method for performing the image quality improvement process by using layer information included in the design data.

FIG. 24 is a schematic diagram showing an example of a method for performing the image quality improvement process by using the layer information included in the design data. The diagram 2401 in FIG. 24 shows a cross section of the sample, wherein the z-axis represents the height direction. The reference characters 2421, 2422 and 2423 represent the first, second and third layers from the top. The reference characters 2411 and 2412 represent contact holes. The hole 2411 connects the top layer 2421 and the second layer 2422. The hole 2412 connects the top layer 2421 and the third layer 2423. While the reference character 2414 also represent contact holes connecting the top layer 2421 and the second layer 2422, a short circuit 2413 has occurred between the two holes.

The images 2402 and 2403 in FIG. 24 are examples of the captured image and the quality-improved image corresponding to the sample 2401, respectively. In the images 2402 and 2403, holes filled in with black represent low average brightness, holes filled in with white represent high average brightness, and a hole filled in with hatching represents intermediate average brightness. In the example of the captured image 2402, the average brightness of the hole 2432 connecting to the third layer is displayed high and thus the hole 2432 can easily be discriminated from the other holes. On the other hand, it is difficult to discriminate the shorted-out holes 2433 from other non-shorted holes. However, observing shorted-out holes with high definition often becomes necessary depending on the purpose.

To meet this request, it is possible, by using the layer information included in the design data, to set high definition enhancement intensity to the holes connecting the top layer and the second layer so that uniformly high contrast difference (i.e., high definition) can be achieved, while setting low definition enhancement intensity to the hole 2432 connecting the top layer and the third layer so that the contrast of the hole becomes close to that of the hole 2431 (i.e., so as to suppress the definition), for example. With this method, the shorted-out holes can be displayed clearly as in the quality-improved image 2403. While the second and third layers from the top are invisible and unrecognizable in the captured image, it is possible to enhance the definition of the observation object under consideration by use of such information on the layers not displayed in the captured image.

Figure 25:
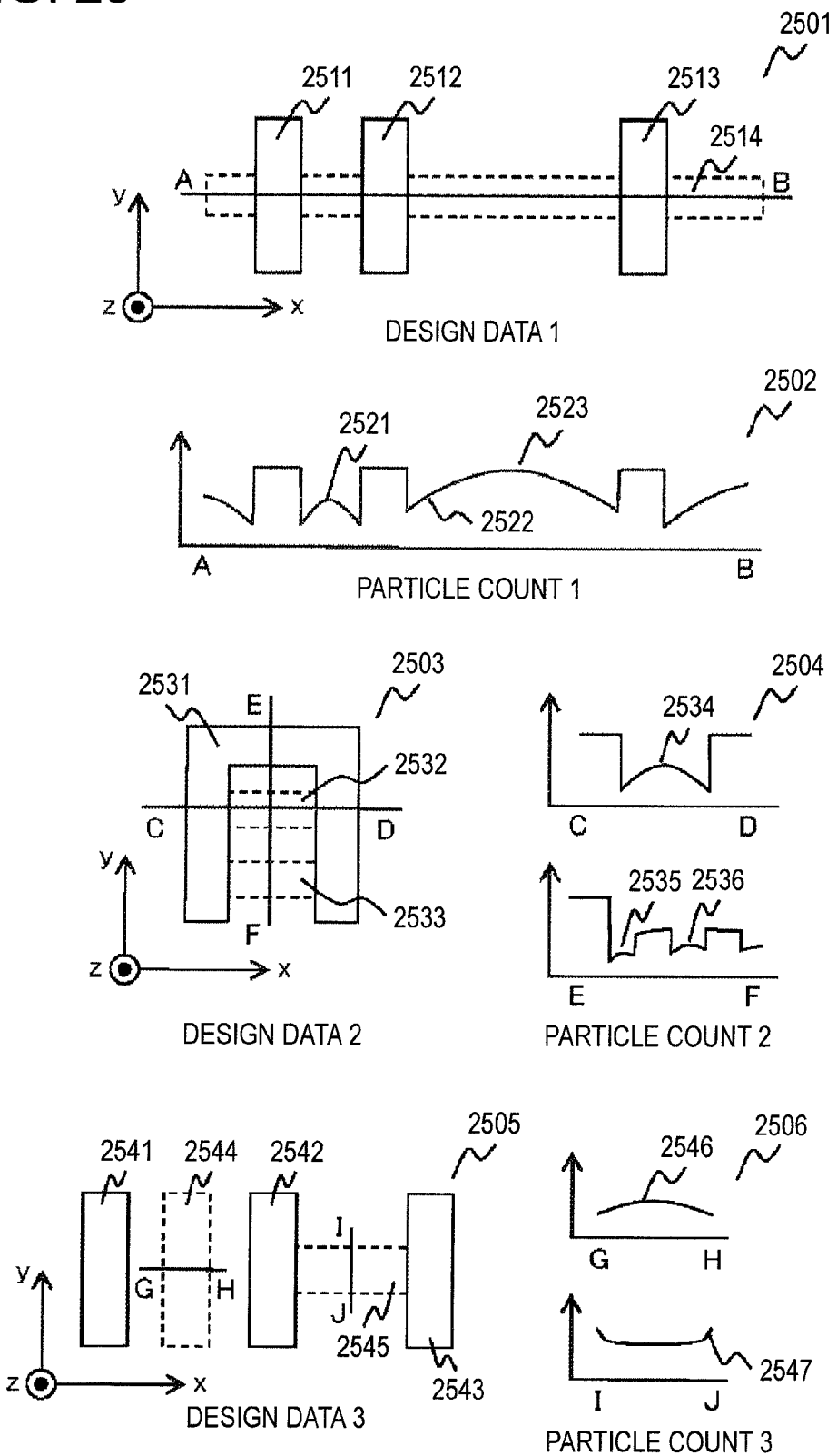
FIG. 25 is a schematic diagram showing an example of the relationship between the shapes of patterns and the amount of detected particles.

FIG. 25 is a schematic diagram showing an example of the relationship between the shapes of patterns and the amount of detected particles. In FIG. 25, the samples are assumed to have the same electrical properties and material properties for the simplicity of the explanation. The diagrams 2501, 2503 and 2505 are examples of the design data.

In the example 2501, a lower layer pattern 2514 in the crosswise direction exists beneath upper layer patterns 2511, 2512 and 2513 in the lengthwise direction. The diagram 2502 shows the amounts of detected particles (particle counts) at positions on a line segment AB in the design data 2501. The particle count from an upper layer pattern is generally higher than that from a lower layer pattern. The particle count is higher at the position 2523 far from the upper layer patterns 2512 and 2513 compared to the position 2522 in the vicinity of an the upper layer pattern 2512. Since the position 2523 is sufficiently far from the upper layer patterns 2512 and 2513, the particles emitted from the sample (position 2523) hardly collides with any upper layer pattern, leading to a particle count substantially equal to that from each upper layer pattern 2512 and 2513. At the position 2521 having more upper layer patterns 2511 and 2512 in its vicinity, the particle count is lower compared to the position 2523 having relatively less upper layer patterns in its vicinity.

In the example 2503, lower layer patterns 2532 and 2533 in the crosswise direction exist beneath an upper layer pattern 2531. The diagram 2504 shows the particle counts at positions on line segments CD and EF in the design data 2503. As indicated by the curve 2534, the particle count from the lower layer pattern is lower than that from the upper layer pattern and the particle count increases with the increase in the distance from the upper layer pattern since the particles emitted from the sample collide less with the upper layer pattern. Referring to the design data 2503, the position 2535 (shown in the diagrams 2504) is close to the upper layer pattern 2531 in three directions (rightward, leftward and upward in FIG. 25), whereas the position 2536 is relatively farther from the upper layer pattern in the upward direction in FIG. 25. Thus, the probability of the collision of a particle emitted from the sample with the upper layer pattern is higher at the position 2535 compared to the position 2536. Consequently, the particle count at the position 2535 is lower than that at the position 2536.

In the example 2505, there exist upper layer patterns 2541, 2542 and 2543 in the lengthwise direction. In the intervals of the upper layer patterns, there exist a lower layer patterns 2544 in the lengthwise direction and a lower layer patterns 2545 in the crosswise direction. The diagram 2506 shows the particle counts at positions on line segments GH and IJ in the design data 2505. At the positions on the line segment GH, the distance from the upper layer pattern changes depending on the position and the particle count decreases with the decrease in the distance. On the other hand, at the positions on the line segment IJ, the distance from the upper layer pattern is constant. However, it is well known that the amount of particles emitted from the sample generally increases in the vicinity of edges of patterns. Thus, the particle count also increases in the vicinity of the edges.

The amount of particles (emitted from the sample and) reaching the detector is greatly affected by the probability of the collision of an emitted particle with the sample. The probability of the collision of a charged particle with the sample is determined by the heights of patterns in the vicinity of the charged particle irradiation position relative to the height of the irradiation position, the distances between the irradiation position and high patterns, the density of the high patterns, etc. Therefore, the amount of the emitted particles detected by the detector (particle count) can be estimated by use of the height information, the design data regarding neighboring positions, and/or information from the captured image. In the present invention, the definition enhancement intensity is set higher for parts where the particle count is lower, for example, by taking advantage of the above properties. By such a process, the visibility of low definition areas can be improved.

While the present invention made by the present inventors has been described specifically above with reference to the embodiments, it goes without saying that the present invention is not to be restricted to the particular illustrative embodiments and a variety of modifications can be made to the configuration and details of the present invention without departing from the spirit and scope of the present invention.

The present embodiment is therefore to be considered in all respects as illustrative and not restrictive, the scope of the invention being indicated by the appended claims, rather than by the foregoing description, and all changes which come within the meaning and range of equivalency of the claims are therefore intended to be embraced therein.

DESCRIPTION OF REFERENCE CHARACTERS

101 design data loading process
102 captured image acquisition process
103 area partitioning process
104 definition enhancement intensity calculation process
105 image quality improvement process
201 alignment process for aligning design data and a captured image
202 design data transformation process
203 area partitioning process
204 present definition calculation process
205 definition enhancement intensity calculation process
301 imaging device
302 charged particle gun
303 charged particle beam
304 condenser lens
305 object lens
306 sample
307 stage
308 detector

309 image generator
321 input/output unit
322 control unit
323 processing unit
324 storage unit
325 image quality improvement unit
331 design data loading unit
332 area partitioning unit
333 definition enhancement intensity calculation unit
334 image quality improvement processing unit

The invention claimed is:

1. A method for inspecting a sample using a charged-particle microscope device, comprising:
   acquiring a captured image by irradiating the sample with charged particles and detecting particles of the same or different type emitted from the sample;
   partitioning the captured image into a plurality of local areas;
   calculating definition enhancement intensity for each of the local areas based on height information on the sample;
   image processing the captured image partitioned into the plurality of local areas using the definition enhancement intensity; and
   inspecting the sample using the image-processed captured image.

2. The method for inspecting a sample using a charged-particle microscope device according to claim 1, further comprising loading design data corresponding to the captured image acquired, wherein height information on the sample is acquired from the loaded design data.

3. The method for inspecting a sample using a charged-particle microscope device according to claim 1, wherein in the calculation of the definition enhancement intensity, the definition enhancement intensity for a partitioned local area including at least one layer other than a top layer in the design data is calculated using layer information on layers existing above the layer under consideration.

4. The method for inspecting a sample using a charged-particle microscope device according to claim 1, comprising calculating present definition from the captured image, and the image processing of the captured image partitioned into the plurality of local areas is executed using the definition enhancement intensity and the present definition.

5. The method for inspecting a sample using a charged-particle microscope device according to claim 4, wherein image processing comprises setting a constraint condition on the definition enhancement intensity using the present definition and the image processing is executed according to the set constraint condition.

6. The method for inspecting a sample using a charged-particle microscope device according to claim 1, wherein height information on the sample estimated from the captured image is used as the height information on the sample.

7. The method for inspecting a sample using a charged-particle microscope device according to claim 6, wherein the height information on the sample is estimated using contour information on the sample calculated from the captured image.

8. The method for inspecting a sample using a charged-particle microscope device according to claim 1, wherein present definition is calculated from the captured image and the image processing of the captured image partitioned into the plurality of local areas is executed using the definition enhancement intensity and the present definition.

9. The method for inspecting a sample using a charged-particle microscope device according to claim 8, comprising setting a constraint condition on the definition enhancement intensity using the present definition and the image processing is executed according to the set constraint condition.

* * * * *